(12) United States Patent
Seth et al.

(10) Patent No.: US 9,290,534 B2
(45) Date of Patent: Mar. 22, 2016

(54) OLIGOMERIC COMPOUNDS HAVING AT LEAST ONE NEUTRALLY LINKED TERMINAL BICYCLIC NUCLEOSIDE

(75) Inventors: Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 1030 days.

(21) Appl. No.: 12/934,498

(22) PCT Filed: Apr. 3, 2009

(86) PCT No.: PCT/US2009/039438
§ 371 (c)(1),
(2), (4) Date: Feb. 2, 2011

(87) PCT Pub. No.: WO2009/124238
PCT Pub. Date: Oct. 8, 2009

(65) Prior Publication Data
US 2011/0130441 A1   Jun. 2, 2011

Related U.S. Application Data

(60) Provisional application No. 61/042,325, filed on Apr. 4, 2008.

(51) Int. Cl.
C07H 21/00  (2006.01)

(52) U.S. Cl.
CPC ....................................... C07H 21/00 (2013.01)

(58) Field of Classification Search
CPC ............ C12N 15/113; C12N 15/1136; C12N 2310/11; C07H 21/00
See application file for complete search history.

(56) References Cited

U.S. PATENT DOCUMENTS

| | | |
|---|---|---|
| 3,687,808 A | 8/1972 | Merigan, Jr. |
| 4,415,732 A | 11/1983 | Caruthers |
| 4,458,066 A | 7/1984 | Caruthers |
| 4,469,863 A | 9/1984 | Tso |
| 4,476,301 A | 10/1984 | Imbach |
| 4,500,707 A | 2/1985 | Caruthers |
| 4,668,777 A | 5/1987 | Caruthers et al. |
| 4,725,677 A | 2/1988 | Koster |
| 4,845,205 A | 7/1989 | Huynh Dinh et al. |
| 4,973,679 A | 11/1990 | Caruthers |
| 4,981,957 A | 1/1991 | Lebleu |
| 5,013,830 A | 5/1991 | Ohtsuka |
| 5,023,243 A | 6/1991 | Tullis |
| 5,034,506 A | 7/1991 | Summerton |
| 5,118,800 A | 6/1992 | Smith |
| 5,130,302 A | 7/1992 | Spielvogel |
| 5,132,418 A | 7/1992 | Caruthers |
| 5,134,066 A | 7/1992 | Rogers |
| RE34,069 E | 9/1992 | Koster et al. |
| 5,149,797 A | 9/1992 | Pederson |
| 5,166,315 A | 11/1992 | Summerton |
| 5,175,273 A | 12/1992 | Bischofberger |
| 5,177,196 A | 1/1993 | Meyer, Jr. |
| 5,177,198 A | 1/1993 | Spielvogel |
| 5,185,444 A | 2/1993 | Summerton |
| 5,188,897 A | 2/1993 | Suhadolnik |
| 5,194,599 A | 3/1993 | Froehler |
| 5,214,134 A | 5/1993 | Weis |
| 5,216,141 A | 6/1993 | Benner |
| 5,220,007 A | 6/1993 | Pederson |
| 5,223,618 A | 6/1993 | Cook et al. |
| 5,235,033 A | 8/1993 | Summerton |
| 5,256,775 A | 10/1993 | Froehler |
| 5,264,423 A | 11/1993 | Cohen |
| 5,264,562 A | 11/1993 | Matteucci |
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,319,080 A | 6/1994 | Leumann |
| 5,321,131 A | 6/1994 | Agrawal |
| 5,359,044 A | 10/1994 | Cook |
| 5,366,878 A | 11/1994 | Pederson |
| 5,367,066 A | 11/1994 | Urdea |
| 5,378,825 A | 1/1995 | Cook |
| 5,386,023 A | 1/1995 | Sanghvi |
| 5,393,878 A | 2/1995 | Leumann |
| 5,399,676 A | 3/1995 | Froehler |
| 5,403,711 A | 4/1995 | Walder et al. |

(Continued)

FOREIGN PATENT DOCUMENTS

| | | |
|---|---|---|
| WO | WO 94/02499 | 2/1994 |
| WO | WO 94/17093 | 8/1994 |

(Continued)

OTHER PUBLICATIONS

Barany, "A New Amino Protecting Group Removable by Reduction. Chemistroy of Dithiasuccinoyl (Dts) Function" J. Am. Chem. Soc. (1977) 99:1763.
Barany, "Kinetics and Mechanism of the Thiolytic Removal of the Dithiasuccinoyl (Dts) Amino Protecting Group" J. Am. Chem. Soc. (1980) 102:3084.
Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48(12):2223-2311.

(Continued)

*Primary Examiner* — Jon E Angell
(74) *Attorney, Agent, or Firm* — McNeil Baur PLLC

(57) ABSTRACT

The present disclosure describes oligomeric compounds having at least one bicyclic nucleoside attached to the 3' or 5' termini by a neutral internucleoside linkage and methods of using the oligomeric compounds. In some embodiments, the oligomeric compounds provided herein hybridize to a portion of a target RNA resulting in loss of normal function of the target RNA.

26 Claims, No Drawings

(56) References Cited

U.S. PATENT DOCUMENTS

| | | | |
|---|---|---|---|
| 5,405,938 A | 4/1995 | Summerton | |
| 5,405,939 A | 4/1995 | Suhadolnik | |
| 5,432,272 A | 7/1995 | Benner | |
| 5,434,257 A | 7/1995 | Matteucci | |
| 5,446,137 A | 8/1995 | Maag | |
| 5,453,496 A | 9/1995 | Caruthers | |
| 5,455,233 A | 10/1995 | Spielvogel | |
| 5,457,187 A | 10/1995 | Gmeiner | |
| 5,459,255 A | 10/1995 | Cook | |
| 5,466,677 A | 11/1995 | Baxter | |
| 5,466,786 A | 11/1995 | Buhr | |
| 5,470,967 A | 11/1995 | Huie | |
| 5,476,925 A | 12/1995 | Letsinger | |
| 5,484,908 A | 1/1996 | Froehler | |
| 5,489,677 A | 2/1996 | Sanghvi | |
| 5,491,133 A | 2/1996 | Walder | |
| 5,502,177 A | 3/1996 | Matteucci | |
| 5,508,270 A | 4/1996 | Baxter | |
| 5,514,785 A | 5/1996 | Van Ness | |
| 5,519,126 A | 5/1996 | Hecht | |
| 5,519,134 A | 5/1996 | Acevedo | |
| 5,525,711 A | 6/1996 | Hawkins | |
| 5,527,899 A | 6/1996 | Froehler | |
| 5,536,821 A | 7/1996 | Agrawal | |
| 5,541,306 A | 7/1996 | Agrawal | |
| 5,541,307 A | 7/1996 | Cook | |
| 5,550,111 A | 8/1996 | Suhadolnik | |
| 5,552,540 A | 9/1996 | Haralambidis | |
| 5,561,225 A | 10/1996 | Maddry | |
| 5,563,253 A | 10/1996 | Agrawal | |
| 5,565,350 A | 10/1996 | Kmiec | |
| 5,565,555 A | 10/1996 | Froehler | |
| 5,567,811 A | 10/1996 | Misiura | |
| 5,571,799 A | 11/1996 | Tkachuk | |
| 5,576,427 A | 11/1996 | Cook | |
| 5,587,361 A | 12/1996 | Cook | |
| 5,587,469 A | 12/1996 | Cook | |
| 5,591,722 A | 1/1997 | Montgomery | |
| 5,594,121 A | 1/1997 | Froehler | |
| 5,596,086 A | 1/1997 | Matteucci | |
| 5,596,091 A | 1/1997 | Switzer | |
| 5,597,909 A | 1/1997 | Urdea | |
| 5,602,240 A | 2/1997 | De Mesmaeker | |
| 5,608,046 A | 3/1997 | Cook | |
| 5,610,289 A | 3/1997 | Cook | |
| 5,610,300 A | 3/1997 | Altmann | |
| 5,614,617 A | 3/1997 | Cook | |
| 5,618,704 A | 4/1997 | Sanghvi | |
| 5,623,065 A | 4/1997 | Cook | |
| 5,623,070 A | 4/1997 | Cook | |
| 5,625,050 A | 4/1997 | Beaton | |
| 5,627,053 A | 5/1997 | Usman et al. | |
| 5,639,873 A | 6/1997 | Barascut | |
| 5,645,985 A | 7/1997 | Froehler | |
| 5,646,265 A | 7/1997 | McGee | |
| 5,652,355 A | 7/1997 | Metelev | |
| 5,652,356 A | 7/1997 | Agrawal | |
| 5,658,873 A | 8/1997 | Bertsch-Frank et al. | |
| 5,663,312 A | 9/1997 | Chaturvedula | |
| 5,670,633 A | 9/1997 | Cook | |
| 5,672,697 A | 9/1997 | Buhr et al. | |
| 5,681,941 A | 10/1997 | Cook | |
| 5,700,920 A | 12/1997 | Altmann | |
| 5,700,922 A | 12/1997 | Cook | |
| 5,721,218 A | 2/1998 | Froehler | |
| 5,750,692 A | 5/1998 | Cook | |
| 5,763,588 A | 6/1998 | Matteucci | |
| 5,792,847 A | 8/1998 | Buhr et al. | |
| 5,830,653 A | 11/1998 | Froehler | |
| 6,005,096 A | 12/1999 | Matteucci | |
| 6,268,490 B1 | 7/2001 | Imanishi et al. | |
| 6,426,220 B1 | 7/2002 | Bennett et al. | |
| 6,600,032 B1 | 7/2003 | Manoharan et al. | |
| 6,770,748 B2 | 8/2004 | Imanishi et al. | |
| 6,794,499 B2 | 9/2004 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 2003/0082807 A1 | 5/2003 | Wengel | |
| 2003/0207841 A1 | 11/2003 | Kaneko et al. | |
| 2003/0224377 A1 | 12/2003 | Wengel et al. | |
| 2004/0014959 A1 | 1/2004 | Sorensen et al. | |
| 2004/0143114 A1 | 7/2004 | Imanishi et al. | |
| 2004/0171570 A1 | 9/2004 | Allerson et al. | |
| 2004/0192918 A1 | 9/2004 | Imanishi et al. | |
| 2004/0219565 A1 | 11/2004 | Kauppinen et al. | |
| 2005/0053981 A1* | 3/2005 | Swayze et al. ............ 435/6 |

FOREIGN PATENT DOCUMENTS

| | | |
|---|---|---|
| WO | WO 99/14226 | 3/1999 |
| WO | WO 2005/121371 | 12/2005 |
| WO | WO 2005/121372 | 12/2005 |
| WO | WO 2007/064853 | 6/2007 |
| WO | WO 2007/134181 | 11/2007 |
| WO | WO 2008/150729 | 12/2008 |
| WO | WO 2008/154401 | 12/2008 |
| WO | WO 2009/006478 | 1/2009 |

OTHER PUBLICATIONS

Beaucage et al., "The Functionalization of Oligonucleotides Via Phosphoramidite Derivatives" Tetrahedron (1993) 49(10):1925-1963.

Beaucage et al., "The Synthesis of Specific Ribonucleotides and Unrelated Phosphorylated Biomolecules by the Phosphoramidite Method" Tetrahedron (1993) 49(46):10441-10488.

Brazma et al., "Gene expression data analysis" FEBS Lett. (2000) 480:17-24.

Burgess et al., "Synthesis of an Oxyamide linked Nucleotide Dimer and Incorporation into Antisense Oligonucleotide Sequences" J. Chem. Soc. Chem. Commun. (1994) 915-916.

Carulli et al., "High Throughput Analysis of Differential Gene Expression" J. Cell. Biochem. Suppl. (1998) 31:286-296.

Caulfield et al., "Achiral internucleoside linkages: CH2-CH2-NH and nH-CH2-CH2 linkages" Bioorg. Med. Chem. Lett. (1993) 3:2771-2776.

Celis et al., "Gene expression profiling: monitoring transcription and translation products using DNA microarrays and proteomics" FEBS Lett (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

Dabkowski et al., "New general synthesis of organophosphorus P-F compounds via reaction of azolides of phosphorus acids with acyl fluorides: novel route to 2-deoxynucleosidyl phosphorofluoridates and phosphorodifluoridates" J. Chem. Soc. Perkins Trans. 1 (1994) 7:817-820.

De Mesmaeker et al., "Amides as a New Type of Backbone Modification in Oligonucleotides" Chem. Int. Ed. Engl. (1994) 33:226-229.

De Mesmaeker et al., "Comparison of Rigid and Flexible Backbones in Antisense Oligonucleotides" J. Bioorg. Med. Chem. Lett. (1994) 4(3):395-398.

Elbashir et al., "Duplexes of 21-nucleotide RNAs mediate RNA interference in cultured mammalian cells" Nature (2001) 411:494-498.

Elbashir et al., "RNA interference is mediated by 21- and 22-nucleotide RNAs" Genes Dev. (2001) 15:188-200.

Englisch et al., "Chemically Modified Oligonucleotides as Probes and Inhibitors" Angewandte Chemie, International Edition (1991) 30:613.

Fire et al., "Potent and Specific Genetic Interference by Double-Stranded RNA in Caenorhabditis Elegans" Nature (1998) 391:806-811.

Fuchs et al., "Identification of Differentially Expressed Genes by Mutually Subtracted RNA Fingerprinting" Anal. Biochem. (2000) 286:91-98.

Gait et al., Applications of Chemically Synthesized RNA in RNA: Protein Interactions, Ed. Smith (1998) 1-36.

(56) References Cited

OTHER PUBLICATIONS

Gallo et al., "2'-C-Methyluridine phosphoramidite: a new building block for the preparation of RNA analogues carrying the 2'-hydroxyl group" Tetrahedron (2001) 57:5707-5713.
Going et al., "Molecular Pathology and Future Developments" Eur. J. Cancer. (1999) 35:1895-1904.
Gogoi et al., "Sugar-thioacetamide backbone in oligodeoxyribonucleosides for specific recognition of nucleic acids" Chem. Commun. (2006) 2373-2375.
Hakansson et al., "Convenient Synthesis of 7-Hydroxy1-1-(hydroxymethyl)-3-(thymin-1-yl)-2,5-dioxabicyclo[2.2.1]hepatanes: alpha-L-Ribo- and Alpha-L-Xylo-Configured LNA Nucleosides" J. Org. Chem. (2000) 65:5161-5166.
Huang et al., "Selective Protection and Deprotection Procedures for Thiol and Hydroxyl Groups" Synlett. (1993) 1:83-84.
Jones et al., "Synthesis and Binding Properties of Pyrimidine Oligodeoxynucleoside Analogs Containing Neutral Phosphodiester Replacements: The Formacetal and 3'-Thioformacetal Internucleoside Linkages" J. Org. Chem. (1993) 58:2983-2991.
Jurecic et al., "Long-distance DD-PCR and cDNA microarrays" Curr. Opin. Microbiol. (2000) 3:316-321.
Kawai et al., "Solid-phase synthesis and hybridization properties of DNA containing sulfide-linked dinucleosides" Nucleic Acids Res. (1993) 21(6):1473-1479.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Koshkin et al., "A Simplified and Efficient Route to 2'-O, 4'-C-Methylene-Linked Bicyclic Ribonucleosides (Locked Nucleic Acid)" J. Org. Chem. (2001) 66:8504-8512.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Kutterer et al., "Synthesis and hybridization studies of urea and carbamate linked thymidine dimers incorporated into oligodeoxynucleosides" Bioorg. Med. Chem. Lett. (1994) 3:435-438.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotechnol. (2000) 80:143-157.
Lauritsen et al., "Oligodeoxynucleotides containing amide-linked LNA-type dinucleotides: synthesis and high-affinity nucleic acid hybridization" Chem. Commun. (2002) 530-532.
Madden et al., "Serial analysis of gene expression: from gene discovery to target identification" Drug Discov. Today (2000) 5:415-425.
McElroy et al., "Synthesis and physicalical properties of sulfonamide-containing oligonucleotides" Bioorg. Med. Chem. Lett. (1994) 4:1071-1076.
Meng et al., "A Sulfide-Linked Oligonucleotide Analogue with Selective Hybridization Properties" J. Angew. Chem. Int. Ed. (1993) 32:729-731.
Montgomery et al., "RNA as a target of double-stranded RNA-mediated genetic interference in Caenorhabditis elegans" PNAS (1998) 95:15502-15507.
Nishikura et al., "A Short Primer on RNAi: RNA-Directed RNA Polymerase Acts as a Key Catalyst" Cell (2001) 107:415-416.

Pannecouque et al., "Synthesis, Enzymatic Stability and Physicochemical Properties of Oligonucleotides Containing A N-Cyanoguanidine Linkage" Tetrahedron (1994) 50:7231-7246.
Peoc'h et al., "Synthesis of 2'-Substituted MMI Linked Nucleosidic Dimers: An Optimization Study in Search of High Affinity Oligonucleotides for Use in Antisense Constructs" Nucleosides, Nucleotides & Nucleic Acids (2004) 23:411-438.
Prashar, "READS: A Method for Display of 3'-End Fragments of Restriction Enzyme-Digested cDNAs for Analysis of Differential Gene Expression" Methods Enzymol. (1999) 303:258-272.
Saha et al., "The synthesis of modified achiral internucleoside linkages: -NHCH2CH2- linked oligonucleosides" Tetrahedron Lett. (1993) 34:6017-6020.
Sanghvi et al., "Synthesis and Structure of Methylene(Dimethylhydrazo) Linked Thymidine Dimer and Their Utility as Antisense Oligonucleotides" Collect. Czech. Chem. Commun. Special Issue (1993) 58:158162.
Sanghvi et al., "Concept, Discovery and Development of MMI Linkage: Story of a Novel Linkage for Antisense Constructs" Nucleosides & Nucleotides (1997) 16:907-916.
Sanghvi et al., "Towards Secong-Generation Synthetic Backbones for Antisense Oligonucleotides" Nucleosides & Nucleotides as Antitumor and Antiviral Agents; Chu & Baker eds., Plenum Press: New York, 1993, pp. 311-324.
Sanghvi, Antisense Research & Applications, Chapter 15, Crooke and Lebleu ed. CRC Press, 1993.
Scaringe, "RNA Oligonucleotide Synthesis via 5'-Sily1-2'-Orthoester Chemistry" Methods (2001) 23:206-217.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Sutcliffe et al., "TOGA: An automated parsing technology for analyzing expess on of nearly all genes" PNAS (2000) 97:1976-1981.
Tabara et al., "RNAi in C. elegans: Soaking in the Genome Sequence" Science (1998) 282:430-431.
Tijsterman et al., "RNA Helicase MUT-14-Dependent Gene Silencing Triggered in C. elegans by Short Antisense RNAs" Science (2002) 295:694-697.
Timmons et al., "Specific interference by ingested dsRNA" Nature (1998) 395:854.
Timmons et al., "Ingestion of bacterially expressed dsRNAs can produce specific potent genetic interference in Caenorhabditis elegans" Gene (2001) 263:103-112.
To, "Identification of Differential Gene Expression by High Throughput Analysis" Comb. Chem. High Throughput. Screen (2000) 3:235-241.
Tuschl et al., "Targeted mRNA degradation by double-stranded RNA in vitro" Genes Dev. (1999) 13:3191-3197.
Wahlestedt et al., "Potent and nontoxic antisense oligonucleotide containing locked nucleic acids" Proc. Natl. Acad. Sci. USA (2000) 97: 5633-5638.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US2009/039438 dated Sep. 10, 2009.

* cited by examiner

SEQUENCE LISTING

<160> NUMBER OF SEQ ID NOS: 6

<210> SEQ ID NO 1
<211> LENGTH: 3160
<212> TYPE: DNA
<213> ORGANISM: H. Sapiens

```
<400> SEQUENCE: 1
cctcccctcg cccggcgcgg tcccgtccgc ctctcgctcg cctcccgcct cccctcggtc      60
ttccgaggcg cccgggctcc cggcgcggcg gcggaggggg cgggcaggcc ggcgggcggt     120
gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300 gccccctctca gcgcctgtga gcagccgcgg gggcagcgcc ctcggggagc cggccggcct     360
gcggcggcgg cagcggcggc gtttctcgcc tcctcttcgt cttttctaac cgtgcagcct     420
cttcctcggc ttctcctgaa agggaaggtg gaagccgtgg gctcgggcgg gagccggctg     480
aggcgcggcg gcggcggcgg cggcacctcc cgctcctgga gcgggggggga gaagcggcgg     540 cggcggcggc cgcggcggct gcagctccag ggagggggtc tgagtcgcct gtcaccattt     600
ccagggctgg gaacgccgga gagttggtct ctccccttct actgcctcca acacggcggc     660
ggcggcggcg gcacatccag ggacccgggc cggttttaaa cctcccgtcc gccgccgccg     720 cacccccgt ggcccgggct ccggaggccg ccggcggagg cagccgttcg gaggattatt     780
cgtcttctcc ccattccgct gccgccgctg ccaggcctct ggctgctgag gagaagcagg     840
cccagtcgct gcaaccatcc agcagccgcc gcagcagcca ttacccggct gcggtccaga     900
gccaagcggc ggcagagcga ggggcatcag ctaccgccaa gtccagagcc atttccatcc     960
tgcagaagaa gccccgccac cagcagcttc tgccatctct ctcctccttt tcttcagcc    1020 acaggctccc agacatgaca gccatcatca aagagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac ataacccac    1320 cacagctaga acttatcaaa ccccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taagacaaa gccaaccgat    2040 acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atcagagaa tgaaccttt gatgaagatc    2220 agcatacaca aattacaaaa gtctgaattt tttttatca gagggataa acaccatga    2280 aaataaactt gaataaactg aaaatggacc ttttttttt taatggcaat aggacattgt    2340
```

-continued

```
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatataccct tttgtgtcaa aaggacattt aaaattcaat taggattaat aaagatggca    2520
ctttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160
```

```
<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                          26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                           25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                      30

<210> SEQ ID NO 5
<211> LENGTH: 12
<212> TYPE: DNA
<213> ORGANISM: Artificial Sequence
<220> FEATURE:
<223> OTHER INFORMATION: Synthetic oligonucleotide
<221> NAME/KEY: misc_feature
<222> LOCATION: 1
<223> OTHER INFORMATION: bases at these positions are RNA

<400> SEQUENCE: 5
uggtccagag cc                                                         12
```

```
<210> SEQ ID NO 6
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 6
tggtccagag cc                                                              12
```

OLIGOMERIC COMPOUNDS HAVING AT LEAST ONE NEUTRALLY LINKED TERMINAL BICYCLIC NUCLEOSIDE

CROSS REFERENCED TO RELATED APPLICATIONS

This application is a U.S. National Phase filing under 35 U.S.C. 371 claiming priority to International Serial No. PCT/US2009/039438 filed Apr. 3, 2009, which is an international application claiming priority to U.S. Provisional Application No. 61/042,325, filed Apr. 4, 2008, each of which is incorporated herein by reference in its entirety.

FIELD OF THE INVENTION

The present disclosure relates to the design, synthesis and application of oligomeric compounds having at least one neutrally linked terminal bicyclic nucleoside. More particularly, the present disclosure provides oligomeric compounds wherein at least one of the termini is a bicyclic nucleoside that is linked via a neutral internucleoside linkage to the oligomeric compound and compositions prepared therefrom. In certain embodiments, the neutrally linked terminal nucleoside contains a 4'-$(CH_2)_n$—O-2' bridge wherein n is 1 or 2. Methods are also provided where a cell is contacted with at least one oligomeric compound of the present disclosure that is complementary to a target RNA resulting in loss of normal function of the target RNA.

SEQUENCE LISTING

The present application is being filed along with a Sequence Listing in electronic format. The Sequence Listing is provided as a file entitled CHEM0034WOSEQ.txt, created on Apr. 1, 2009 which is 8 Kb in size. The information in the electronic format of the sequence listing is incorporated herein by reference in its entirety.

BACKGROUND OF THE INVENTION

Antisense technology is an effective means for reducing the expression of one or more specific gene products and can therefore prove to be uniquely useful in a number of therapeutic, diagnostic, and research applications. The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired. Modifications to enhance the effectiveness of the antisense oligonucleotides have taken many forms. These modifications include sugar-phosphate backbone modifications, base ring modifications and sugar moiety modifications.

Modification of oligonucleotides to enhance nuclease resistance generally has taken place on the phosphorus atom of the sugar-phosphate backbone. Phosphorothioates, methyl phosphonates, phosphoramidates and phosphotriesters have been reported to confer various levels of nuclease resistance. Phosphate-modified oligonucleotides, however, generally have suffered from inferior hybridization properties. See, e.g., Cohen, J. S., ed. Oligonucleotides: Antisense Inhibitors of Gene Expression, (CRC Press, Inc., Boca Raton Fla., 1989).

Various dephosphono linkages (linkages without the phosphorus atom) modifications have been synthesized and studied for their antisense properties. Nonionic, achiral amide linkages (De Mesmaeker et al., Chem. Int. Ed. Engl. 1994, 33, 226-229; Just et al., Synlett 1994, 137-139) were disclosed. A full account of the synthesis and properties of the five isomeric amide modifications was described (De Mesmaeker el al., (1994) Novel Backbone Replacements for Oligonucleotides, In Carbohydrate Modifications in Antisense Research; Y. S. Sanghvi and P. D. Cook Eds. ACS Symposium Series 580:24-39). Gogoi et al. presented the synthesis of thioacetamido nucleic acids (TANA) backbone and thermal stability studies with complementary DNA and RNA sequences (Gogoi et al., Chem. Commun., 2006, pp. 2373-2375).

Several nitrogen containing backbone modifications similar to the amides were evaluated as dimeric nucleosides (Sanghvi et al., Nucleosides Nucleotides 1997, 16, pp. 907-916). Peoc'h reported the synthesis of four methylene(methylimino) (MMI) linked oligodeoxyribonucleotide dimers modified at the T-position with fluoro and/or methoxy groups and their incorporation into different sequences (Peoc'h et al., Nucleosides, Nucleotides & Nucleic Acids, 23, pp. 411-438, 2004). Amino linkages have been synthesized and studied for enhanced cellular absorption (Saha el al., Tetrahedron Lett. 1993, 34, 6017-6020; De Mesmaeker el al., J. Bioorg. Med. Chem. Lett. 1994, 4, pp. 395-398; Caulfield et al, Bioorg. Med. Chem. Lett. 1993, 3, pp. 2771-2776). Other nitrogen containing backbones include oxime (Sanghvi et al., In Nucleosides and Nucleotides as Antitumor and Antiviral Agents; C. K. Chu and D. C. Baker Eds.: Plenum Press: New York, 1993, pp. 311-324), methyleneimino (ibid), methyleneoxy(methylimino) (MOMI) (ibid), methylene(dimethylhydrazo) (MDH) (Sanghvi et al., Collect. Czech. Chem. Commun. Special Issue 1993, 58, pp. 158-162), hydroxyl (methyliminomethylene) (HMIM) (Sanghvi et al., 11$^{th}$ IRT Nucleosides & Nucleotides, Leuven, Belgium, Sep. 7-11, 1994 (poster presentation)), carbamate (Dabkowski et al., J Chem. Soc. Perkin Trans. 1 1994, pp. 817-829), oxyamide linkage (Burgess et al., J. Chem. Soc. Chem. Commun. 1994, pp. 915-916), N-substituted guanidine (Vandendrissche et al., J. Chem. Soc. 1993, pp. 1567-1575; Pannecouque et al., Tetrahedron 1994, 50, 7231-7246), urea (Kutterer et al., Bioory. Med. Chem. Lett. 1994, 3, pp. 435-438) and thiourea linkages (Vandendrissche et al., J. Chem. Soc. 1993, pp. 1567-1575).

Synthesis of sulfur-containing backbone modifications, such as sulfonamide (McElroy et al., Bioorg. Med. Chem. Lett. 1994, 4, 1071-1076), sulfamoyl (Dewynter et al., Acad. Sci. 1992, 315, pp. 1675-1682), sulfonate (Huang et al., Synlett 1993, pp. 83-84), sulfide (Wang et al., Chin. Chem. Lett. 1993, 4, pp. 101-104; Huang et al., Synlett 1993, pp. 83-84; Kawai et al., Nucleic Acids Res. 1993, 21, pp. 1473-1479; Meng et al., J. Angew. Chem. Int. Ed. Engl. 1993, 32, pp. 729-731; Just el al. (1994), Synthesis and Hybridization Properties of DNA Oligomers Containing Sulfide-Linked Dinucleosides. In Carbohydrate Modifications in Antisense Research; Y. S. Sanghvi and P. D. Cook Eds. ACS Symposium Series 580; (pp. 52-65)), and sulfone linkages (Just el al. (1994), Synthesis and Hybridization Properties of DNA Oligomers Containing Sulfide-Linked Dinucleosides. In Carbohydrate Modifications in Antisense Research; Y. S. Sanghvi and P. D. Cook Eds. ACS Symposium Series 580; (pp. 62-65)) have been accomplished by several research groups.

Another backbone substitution is the formacetal and the related thioformacetal (Jones et al., J. Org. Chem., 58, pp.

2983-2991, 1993). Matteucci reported the synthesis of oligonucleotide analogs with one or more phosphodiester linkages that are replaced by a formacetal/ketal type linkage (U.S. Pat. No. 5,264,562 filed Apr. 24, 1991).

Chemically modified nucleosides are routinely used for incorporation into antisense sequences to improve the properties of antisense oligonucleotides as an alternative approach. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued U.S. patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety. Many LNA's are toxic. See, e.g., Swayze, E. E.; Siwkowski, A. M.; Wancewicz, E. V.; Migawa, M. T.; Wyrzykiewicz, T. K.; Hung, G.; Monia, B. P.; Bennett, C. F., Antisense oligonucleotides containing locked nucleic acid improve potency but cause significant hepatotoxicity in animals (Nucl. Acids Res., doi: 10.1093/nar/gkl1071, December 2006, advanced online publication).

Amide-linked dimers having one or two LNA nucleosides have been prepared and placed at internal positions within an oligomeric compound to determine their effects on Tm relative to a DNA/RNA duplex (Lauritsen et al., Chem. Commun., 2002, 530-532).

The present disclosure combines and incorporates both the synthesis of modified sugar-phosphate backbone and bicyclic nucleosides in attempting to enhance the properties of antisense oligonucleotides. Disclosed herein are neutral backbone bicyclic nucleic acid dimer analogs and antisense compounds prepared therefrom useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Disclosed herein are oligomeric compounds that comprise at least one terminal bicyclic nucleoside that is linked to the oligomeric compound by a neutral internucleoside linkage. In certain embodiments, the oligomeric compound is from 8 to about 40 monomeric subunits in length. In certain embodiments, the oligomeric compound comprises more than one neutral internucleoside linkage. In certain embodiments, the terminal bicyclic nucleoside can be linked to a conjugate group.

In certain embodiments, at least one neutral internucleoside linkage covalently attaches the bicyclic nucleoside to the 3'-terminus. In certain embodiments, at least one neutral internucleoside linkage covalently attaches the bicyclic nucleoside to the 3'-terminus and the penultimate nucleoside on the 3'-end of the oligomeric compound is also a bicyclic nucleoside.

In certain embodiments, at least one neutral internucleoside linkage covalently attaches the bicyclic nucleoside to the 5'-terminus. In certain embodiments, at least one neutral internucleoside linkage covalently attaches the bicyclic nucleoside to the 3'-terminus and the penultimate nucleoside on the 5'-end of the oligomeric compound is also a bicyclic nucleoside.

In certain embodiments, at least one neutral internucleoside linkage covalently attaches at least one bicyclic nucleoside to the 3'-terminus and at least one neutral internucleoside linkage covalently attaches at least one bicyclic nucleoside to the 5'-terminus. In certain embodiments, at least one neutral internucleoside linkage covalently attaches at least one bicyclic nucleoside to the 3'-terminus, at least one neutral internucleoside linkage covalently attaches at least one bicyclic nucleoside to the 5'-terminus and the penultimate nucleosides on the 5' and 3'-ends of the oligomeric compound are also bicyclic nucleosides.

In certain embodiments, each neutral internucleoside linkage is independently, a phosphotriester, methylphosphonate, MMI (3'-$CH_2$—N($CH_3$)—O-5'), amide-3 (3'-$CH_2$—C(=O)—N(H)-5'), formacetal (3'-O—$CH_2$—O-5') or a thioformacetal (3'-S—$CH_2$—O-5'). In certain embodiments, each neutral internucleoside linkage is independently, a MMI (3'-$CH_2$—N($CH_3$)—O-5'), amide-3 (3'-$CH_2$—C(=O)—N(H)-5'), formacetal (3'-O—$CH_2$—O-5') or a thioformacetal (3'-S—$CH_2$—O-5').

In certain embodiments, each of the bicyclic nucleosides have formula I:

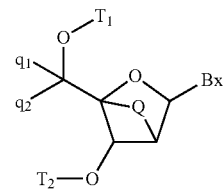

wherein independently for each of said bicyclic nucleosides having formula I:
  Bx is a heterocyclic base moiety;
  $T_1$ and $T_2$ are each independently H, a hydroxyl protecting group, a linked conjugate group, a terminal group, an internucleoside linking group or a neutral internucleoside linking group;
  $q_1$ and $q_2$ are each independently hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $C_5$-$C_{20}$ aryl, substituted $C_5$-$C_{20}$ aryl, acyl, substituted acyl, $C_1$-$C_{12}$ aminoalkyl or substituted $C_1$-$C_{12}$ aminoalkyl;
  Q is a bivalent bridging group comprising from 1 to 8 linked biradical groups independently selected from —O—, —S—, —N($R_1$)—, —C($R_1$)($R_2$)—, —C($R_1$)=C($R_1$)—, —C($R_1$)=N—, —C(=N$R_1$)—, —Si($R_1$)$_2$—, —$SO_2$—, —SO—, C(=O)— and —C(=S)—;

each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1 NJ_1 J_2$, $SJ_1$, $N_3$, $COOJ_1$, acyl (C(=O)—H), substituted acyl, CN, sulfonyl (S(=O)$_2$-$J_1$) or sulfoxyl (S(=O)-$J_1$);

each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group; and wherein each substituted group comprises one or more optionally protected substituent groups independently selected from halogen, $OJ_1$, $NJ_1 J_2$, =$NJ_1$, $SJ_1$, $N_3$, CN, OC(=L)$J_1$, OC(=L)$NJ_1 J_2$ and $NJ_3$C(=L)$NJ_1 J_2$, wherein each $J_1$, $J_2$ and $J_3$ is, independently, H or $C_1$-$C_6$ alkyl, and L is O, S or $NJ_1$.

In certain embodiments, $q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

In certain embodiments, each $R_1$ and $R_2$ is, independently, H, hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$ $NJ_1 J_2$, $SJ_1$, $N_3$, $COOJ_1$, acyl (C(=O)—H), substituted acyl, CN, sulfonyl (S(=O)$_2$-$J_1$) or sulfoxyl (S(=O)-$J_1$).

In certain embodiments, each Q is, independently, 4'-[CH($R_1$)]$_n$—O-2', each $R_1$ is, independently, H, alkyl or substituted alkyl and each n is from 1 to 3. In certain embodiments, each Q is 4'-[CH($R_1$)]$_n$—O-2' wherein each $R_1$ is, independently, H or alkyl and each n is 1 or 2. In certain embodiments, each Q is 4'-[CH($R_1$)]$_n$—O-2' wherein each $R_1$ is, independently, H or methyl and each n is 1 or 2. In certain embodiments, each Q is 4'-[CH($R_1$)]$_n$—O-2' wherein each $R_1$ is, independently, H or methyl and each n is 1.

In certain embodiments, the oligomeric compound further comprises at least one 3' or 5'-linked conjugate group. In certain embodiments, the oligomeric compound further comprises at least one 3' or 5'-linked terminal group.

In certain embodiments, each internucleoside linking group that is not a neutral internucleoside linking group is a phosphodiester. In certain embodiments, each internucleoside linking group that is not a neutral internucleoside linking group is a phosphorothioate. In certain embodiments, each internucleoside linking group that is not a neutral internucleoside linking group is, independently, a phosphodiester or a phosphorothioate. In certain embodiments, each internucleoside linking group that is not a neutral internucleoside linking group is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or boranophosphate.

In certain embodiments, each Bx is, independently, a pyrimidine, substituted pyrimidine, purine or substituted purine. In certain embodiments, each Bx is, independently, uracil, 5-methyluracil, 5-propynyl-uracil, thymine, cytosine, 5-methylcytosine, 5-propynyl-cytosine, adenine or guanine. In certain embodiments, each Bx is, independently, uracil, thymine, cytosine, adenine or guanine. In certain embodiments, each Bx is, independently, uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one.

In certain embodiments, oligomeric compounds are provided comprising a plurality of bicyclic nucleosides of formula I. In certain embodiments, oligomeric compounds are provided comprising at least one region of from 1 to about 5 contiguous bicyclic nucleosides of formula I. In certain embodiments, oligomeric compounds are provided comprising at least one region of from 1 to about 5 contiguous bicyclic nucleosides of formula I wherein each linked monomeric subunit that is not a bicyclic nucleoside having formula I is, independently, a βD-2'-deoxyribonucleoside or a modified nucleoside. In certain embodiments, each of the modified nucleosides is, independently, a 2'-modified nucleoside, a 4'-thio modified nucleoside or a 4'-thio-2'-modified nucleoside.

In certain embodiments, oligomeric compounds are provided comprising at least one region of from 1 to about 5 contiguous bicyclic nucleosides of formula I wherein each linked monomeric subunit that is not a bicyclic nucleosides of formula I is a βD-2'-deoxyribonucleoside.

In certain embodiments, oligomeric compounds are provided comprising at least one region of from 1 to about 5 contiguous bicyclic nucleosides of formula I wherein the oligomeric compound is a blockmer, a 3'-hemimer or 5'-hemimer. In certain embodiments, each monomeric subunit is, independently, a bicyclic nucleosides having formula I or a βD-2'-deoxyribonucleoside.

In certain embodiments, gapped oligomeric compounds are provided comprising two external regions separated by an internal region wherein each external region independently comprises from 1 to 5 contiguous bicyclic nucleosides of formula I and the internal region comprises from 6 to about 23 contiguous monomeric subunits independently selected from nucleosides and modified nucleosides. In certain embodiments, each monomeric subunit in the internal region is, independently, a β-D-2'-deoxyribonucleoside or a modified nucleoside. In certain embodiments, essentially each monomeric subunit in the internal region is a β-D-2'-deoxyribonucleoside.

In certain embodiments, gapped oligomeric compounds are provided wherein the internal region comprises from about 8 to about 12 β-D-2'-deoxyribonucleosides. In certain embodiments, each external region comprises from 1 to 3 bicyclic nucleosides of formula I. In certain embodiments, the internal region comprises from about 10 to about 12 β-D-2'-deoxyribonucleosides.

In certain embodiments, gapped oligomeric compounds are provided wherein the internal region comprises from about 11 to about 18 β-D-2'-deoxyribonucleosides. In certain embodiments, each external region comprises from 1 to 3 bicyclic nucleosides of formula I. In certain embodiments, the internal region comprises from about 12 to about 14 β-D-2'-deoxyribonucleosides.

In certain embodiments, gapped oligomeric compounds are provided wherein each external region independently comprises from 1 to 3 bicyclic nucleosides of formula I. In certain embodiments, each external region comprises 2 bicyclic nucleosides of formula I. In certain embodiments, the internal region comprises 10 β-D-2'-deoxyribonucleosides.

In certain embodiments, gapped oligomeric compounds are provided comprising two external regions separated by an internal region wherein each external region independently comprises from 1 to 5 contiguous bicyclic nucleosides of formula I and the internal region comprises from 6 to about 23 contiguous monomeric subunits independently selected from nucleosides and modified nucleosides and wherein each internucleoside linkage that is not a neutral internucleoside linkage is a phosphodiester. In certain embodiments, each internucleoside linkage that is not a neutral internucleoside linkage a phosphorothioate. each internucleoside linking group that is not a neutral internucleoside linkage is, independently, a phosphodiester or a phosphorothioate. In certain embodiments, each internucleoside linking group that is not a neutral internucleoside linkage is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or boranophosphate.

In certain embodiments, oligomeric compounds are provided comprising from 8 to about 18 linked monomeric subunits. In certain embodiments, oligomeric compounds are provided comprising from 10 to about 16 linked monomeric subunits. In certain embodiments, oligomeric compounds are provided comprising from 10 to about 14 linked monomeric subunits. In certain embodiments, oligomeric compounds are provided comprising from 17 to about 26 linked monomeric subunits. In certain embodiments, oligomeric compounds are provided comprising from 18 to about 21 linked monomeric subunits. In certain embodiments, oligomeric compounds are provided comprising from 19 to about 20 linked monomeric subunits.

Disclosed herein are methods comprising contacting at least one cell with at least one oligomeric compound wherein the oligomeric compound comprises at least one terminal bicyclic nucleoside linked to the oligomeric compound by a neutral internucleoside linkage and wherein the oligomeric compound is complementary to a target RNA. In certain embodiments, the oligomeric compound comprises from about 8 to about 40 linked monomeric subunits. In certain embodiments, the cell(s) is in an animal. In certain embodiments, the cell(s) is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the provided methods further comprise evaluating the antisense activity of the oligomeric compound on the cell. In certain embodiments, the evaluating step comprises detecting the levels of at least one target RNA. In certain embodiments, the evaluating step comprises detecting the levels of at least one protein. In certain embodiments, the evaluating step comprises detecting one or more phenotypic effects.

In certain embodiments, methods are provided comprising providing the oligomeric compounds disclosed herein for use in therapy. In certain embodiments, the therapy is treating a disease characterized by undesired gene expression. In certain embodiments, the therapy is treating a disease by inhibiting gene expression. In certain embodiments, a cell in an animal is to be contacted with one or more of the oligomeric compounds disclosed herein.

In certain embodiments, oligomeric compounds disclosed herein are provided for the manufacture of a medicament for the treatment of a disease characterized by undesired gene expression. In certain embodiments, oligomeric compounds disclosed herein are provided for the manufacture of a medicament for treating a disease by inhibiting gene expression. In certain embodiments, pharmaceutical compositions are provided comprising one or more oligomeric compounds as provided herein and a pharmaceutically acceptable carrier.

DETAILED DESCRIPTION OF THE INVENTION

The present disclosure provides oligomeric compounds having at least one bicyclic nucleoside covalently linked to the 3' or 5' terminus via a neutral internucleoside linkage. In general at least one of the ionizable phosphate residues is replaced with a neutral internucleoside linkage to improve desirable properties including but not limited to enhanced nuclease resistance. A plurality of bicyclic nucleosides can be included in the oligomeric compounds with one or more neutral internucleoside linkages covalently attaching bicyclic nucleosides to other bicyclic nucleosides or to other monomeric subunits comprising the oligomeric compound.

In certain embodiments, oligomeric compounds are provided having one or more bicyclic nucleosides having Formula I:

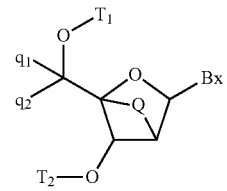

wherein independently for each of said bicyclic nucleosides having formula I:

Bx is a heterocyclic base moiety;

$T_1$ and $T_2$ are each independently H, a hydroxyl protecting group, a linked conjugate group, a terminal group, an internucleoside linking group or a neutral internucleoside linking group;

$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

Q is a bivalent bridging group comprising from 1 to 8 linked biradical groups independently selected from —O—, —S—, —N($R_1$)—, —C($R_1$)($R_2$)—, —C($R_1$)═C($R_1$)—, —C($R_1$)═N—, —C(═N$R_1$)—, —SO$_2$—, —SO—, —C(═O)— and —C(═S)—;

each $R_1$ and $R_2$ is, independently, H, hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$ $NJ_1J_2$, $SJ_1$, $N_3$, $COOJ_1$, acyl (C(═O)—H), substituted acyl, CN, sulfonyl (S(═O)$_2$-$J_1$) or sulfoxyl (S(═O)-$J_1$); and wherein each substituted group comprises one or more optionally protected substituent groups independently selected from halogen, $OJ_1$, $NJ_1J_2$, ═$NJ_1$, $SJ_1$, $N_3$, CN, OC(═L)$J_1$, OC(═L)$NJ_1J_2$ and $NJ_3$C(═L)$NJ_1J_2$, wherein each $J_1$, $J_2$ and $J_3$ is, independently, H or $C_1$-$C_6$ alkyl and L is O, S or $NJ_1$.

In certain embodiments, oligomeric compounds are prepared having a hemimer or gapmer motif wherein from 1 to 5 contiguous bicyclic nucleosides are located at one terminus or both termini respectively and the terminal bicyclic nucleoside at one of the 3' or 5' end is connected to the oligomeric compound by a neutral internucleoside linkage. In another preferred embodiment, the oligomeric compound is a gapmer having the neutral internucleoside linkage at the 5'-terminus. In another preferred embodiment, the oligomeric compound is a gapmer having the neutral internucleoside linkage at the 3'-terminus. In a further preferred embodiment, the oligomeric compound is a gapmer having a neutral internucleoside linkage at the 3'-terminus and a second neutral internucleoside linkage at the 5'-terminus.

Bicyclic nucleosides having Formula I can be prepared in various configurations for incorporation into oligomeric compounds. All possible configurations are envisioned herein with preferred configurations including, but not limited to, βD and α-L. Examples of βD and α-L BNA nucleosides are shown below wherein the 2'-4' bridge exemplified is for illustration and not meant to be limiting.

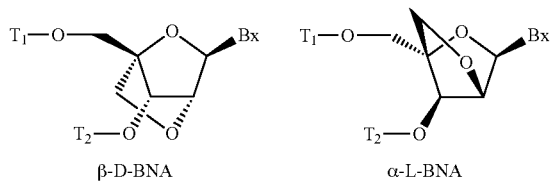

β-D-BNA       α-L-BNA

As used herein the phrase "neutral internucleoside linkage" is intended to include essentially only internucleoside linkages that are non-ionic. Neutral internucleoside linkages include but are not limited to phosphotriesters, methylphosphonates, MMI (3'-CH$_2$—N(CH$_3$)—O-5), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and CH$_2$ component parts.

In certain embodiments, the oligomeric compounds provided herein can be described as having a particular motif. Motifs include without limitation, gapped motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include at least one 5' or 3' terminal group such as for example a conjugate or reporter group. The positioning of the one or more bicyclic nucleosides and the neutral internucleoside linkages as provided herein, the use of linkage strategies and 5' or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar groups. The only determinant for the motif of an oligomeric compound is the differences or lack of differences between the sugar groups. As used herein the term "sugar group" as it applies to motifs includes naturally occurring sugars having a furanose ring, sugars having a modified furanose ring and sugar surrogates wherein the furanose ring has been replaced with another ring system such as for example a morpholino or hexitol ring system. When each sugar group is the same (DNA, RNA, modified or surrogate) the motif is termed uniformly fully modified. When two or more types of sugar groups are present the motif is defined by the pattern created from the positioning of monomer subunits having one type of sugar group relative to the positioning of monomer subunits having different types of sugar groups within an oligomeric compound.

Illustrative examples of some different types of sugar groups useful in the preparation of oligomeric compounds having motifs include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic modified sugars (such as the 2'-O—CH$_2$-4' or 2'-O—(CH$_2$)$_2$-4' bridged ribose derived bicyclic sugars) and sugar surrogates (such as when the ribose ring has been replaced with a morpholino or a hexitol ring system). The type of heterocyclic base and internucleoside linkage used at each position is variable and is not a factor in determining the motif. The presence of one or more other groups including but not limited to capping groups, conjugate groups and other 5' or 3'-terminal groups is also not a factor in determining the motif.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar groups, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, one of A and B is a bicyclic nucleoside as provided herein.

As used herein the term "uniformly fully modified motif" refers to an oligomeric compound comprising a contiguous sequence of linked monomer subunits that each have the same type of sugar group. The heterocyclic base and internucleoside linkage is independently variable at each position. The motif further optionally includes the use of one or more other groups including but not limited to capping groups, conjugate groups and other 5' or 3'-terminal groups. In certain embodiments, the uniformly fully modified motif includes a contiguous sequence of bicyclic nucleosides. In certain embodiments, one or both of the 5' and 3'-ends of the contiguous sequence of bicyclic nucleosides, comprise 5' or 3'-terminal groups such as one or more unmodified nucleosides.

As used herein the term "hemimer motif" refers to an oligomeric compound comprising a contiguous sequence of monomer subunits that each have the same type of sugar group with a further short contiguous sequence of monomer subunits located at the 5' or the 3' end that have a different type of sugar group. The heterocyclic base and internucleoside linkage is independently variable at each position. The motif further optionally includes the use of one or more other groups including but not limited to capping groups, conjugate groups and other 5' or 3'-terminal groups. In general, a hemimer is an oligomeric compound of uniform sugar groups further comprising a short region (1, 2, 3, 4 or about 5 monomer subunits) having uniform but different sugar groups located on either the 3' or the 5' end of the oligomeric compound.

In certain embodiments, the hemimer motif comprises a contiguous sequence of from about 10 to about 28 monomer subunits having one type of sugar group with from 1 to 5 or from 2 to about 5 monomer subunits having a second type of sugar group located at one of the termini. In certain embodiments, the hemimer is a contiguous sequence of from about 8 to about 20 β-D-2'-deoxyribonucleosides having from 1-12 contiguous bicyclic nucleosides located at one of the termini. In certain embodiments, the hemimer is a contiguous sequence of from about 8 to about 20 β-D-2'-deoxyribonucleosides having from 1-5 contiguous bicyclic nucleosides located at one of the termini. In certain embodiments, the hemimer is a contiguous sequence of from about 12 to about 18 β-D-2'-deoxyribonucleosides having from 1-3 contiguous bicyclic nucleosides located at one of the termini. In certain embodiments, the hemimer is a contiguous sequence of from about 10 to about 14 β-D-2'-deoxyribonucleosides having from 1-3 contiguous bicyclic nucleosides located at one of the termini.

As used herein the term "blockmer motif" refers to an oligomeric compound comprising an otherwise contiguous sequence of monomer subunits wherein the sugar groups of each monomer subunit is the same except for an interrupting internal block of contiguous monomer subunits having a different type of sugar group. The heterocyclic base and internucleoside linkage is independently variable at each position of a blocker oligomeric compound. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmer oligomeric compounds are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, each of the two or more regions, independently, have the same or a different type of sugar group. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous bicyclic nucleosides or modified nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is essentially the same. In certain embodiments, each monomer subunit within a particular region has the same sugar group. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising bicyclic nucleosides as disclosed herein. In certain embodiments, the gapped oligomeric compounds comprise an internal region of β-D-2'-deoxyribonucleosides with both of the external regions comprising bicyclic nucleosides as provided herein. In certain embodiments, gapped oligomeric compounds are provided herein wherein all of the monomer subunits comprise non-naturally occurring sugar groups.

In certain embodiments, gapped oligomeric compounds are provided comprising one or two bicyclic nucleosides at the 5'-end, two or three bicyclic nucleosides at the 3'-end and an internal region of from 10 to 16 β-D-2'-deoxyribonucleosides. In certain embodiments, gapped oligomeric compounds are provided comprising one bicyclic nucleosides at the 5'-end, two bicyclic nucleosides at the 3'-end and an internal region of from 10 to 16 β-D-2'-deoxyribonucleosides. In certain embodiments, gapped oligomeric compounds are provided comprising one bicyclic nucleoside at the 5'-end, two bicyclic nucleosides at the 3'-end and an internal region of from 10 to 14 β-D-T-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The gapped oligomeric compounds of the present disclosure include at least one neutral internucleoside linkage which covalently attaches either a 5'-terminal bicyclic nucleoside or a 3'-terminal bicyclic nucleoside to the oligomeric compound. In one aspect there is only one neutral internucleoside linkage that is connecting a 5'-terminal bicyclic nucleoside to the oligomeric compound. In another aspect there is only one neutral internucleoside linkage that is connecting a 3'-terminal bicyclic nucleoside to the oligomeric compound. In a further aspect the oligomeric compound comprises two neutral internucleoside linkages, one connecting a 5'-terminal bicyclic nucleoside to the oligomeric compound and a second connecting a 3'-terminal bicyclic nucleoside to the oligomeric compound. A preferred gapped oligomeric compound according to the present disclosure comprises an internal region of β-D-2'-deoxyribonucleosides with both of the external regions comprising bicyclic nucleosides of formula I. Another preferred gapped oligomeric compound according to the present disclosure comprises an internal region of β-D-2'-deoxyribonucleosides with both of the external regions comprising bicyclic nucleosides of formula I with a neutral internucleoside linkage attaching the 5'-terminal bicyclic nucleoside.

In one aspect of the present disclosure, gapped oligomeric compounds are provided comprising one or two bicyclic nucleosides of formula I at the 5'-end, two or three bicyclic nucleosides of formula I at the 3'-end and an internal region of from 10 to 16 nucleosides. In one aspect of the present disclosure, gapped oligomeric compounds are provided comprising one bicyclic nucleoside of formula I at the 5'-end, two bicyclic nucleosides of formula I at the 3'-end and an internal region of from 10 to 16 nucleosides. In one aspect of the present disclosure, gapped oligomeric compounds are provided comprising one bicyclic nucleoside of formula I at the 5'-end, two bicyclic nucleosides of formula I at the 3'-end and an internal region of from 10 to 14 nucleosides. In one aspect of the present disclosure, gapped oligomeric compounds are provided comprising two bicyclic nucleosides of formula I at the 5'-end, two bicyclic nucleosides of formula I at the 3'-end and an internal region of from 10 to 16 nucleosides. In one aspect of the present disclosure, the internal region is essentially a contiguous sequence of β-D-deoxyribonucleosides. In one aspect of the present disclosure, oligomeric compounds are provided that further include one or more 5'- and/or 3'-terminal groups including but not limited to further modified or unmodified nucleosides, conjugate groups, phosphate moieties and other useful groups known to the art skilled.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino, (—N$R_{bb}R_{cc}$), imino(=N$R_{bb}$), amido (—C(O)N—$R_{bb}R_{cc}$ or —N($R_{bb}$)C(O))$R_{aa}$), azido (—$N_3$), nitro (—$NO_2$), cyano (—CN), carbamido (—OC(O))N$R_{bb}R_{cc}$ or —N($R_{bb}$)C(O))O$R_{aa}$), ureido (—N($R_{bb}$)C(O))N$R_{bb}R_{cc}$), thioureido (—N($R_{bb}$)C(S)N$R_{bb}R_{cc}$), guanidinyl (N($R_{bb}$)C(=N$R_{bb}$)N$R_{bb}R_{cc}$), amidinyl (—C(=N$R_{bb}$)N$R_{bb}R_{cc}$ or —N($R_{bb}$)C(N$R_{bb}$)$R_{aa}$), thiol (—S$R_{bb}$), sulfinyl (—S(O)$R_{bb}$), sulfonyl (—S(O)$_2R_{bb}$), sulfonamidyl (—S(O))$_2$N$R_{bb}R_{cc}$ or —N($R_{bb}$)—S(O)$_2R_{bb}$) and conjugate groups. Wherein each $R_{aa}$, $R_{bb}$ and $R_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

The term "heterocyclic radical," as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used in the present disclosure includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "oxo" refers to the group (=O).

As used herein the terms "bicyclic nucleic acid" and "bicyclic nucleoside" refer to nucleosides wherein the sugar portion of the nucleoside is bicyclic (e.g. bicyclic sugar). In a broader sense the terms include any bicyclic monomer that can be placed into an oligomeric compound that will not inhibit duplex formation and will hybridize to a nucleoside in a target or complementary strand. In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N(O$CH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya, et al., *J. Org. Chem.*, 2009, 74, 118-134); and 4'-$CH_2$—C(=$CH_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

Linking groups or bifunctional linking moieties such as those known in the art are amenable to the present disclosure. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In one aspect of the present disclosure oligomeric compounds are modified by covalent attachment of one or more conjugate groups. In general, conjugate groups modify one or more properties of the attached oligomeric compound including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more 5' or 3'-terminal groups. The terms "5' or 3'-terminal groups", "terminal groups", "5-terminal group" and "3'-terminal group" as used herein are meant to include useful groups known to the art skilled that can be placed on one or both of the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (a group for enhancing uptake and/or delivery) or enhancing one or more other desirable properties of the oligomeric compound (such as for example: nuclease stability, binding affinity, uptake and/or delivery). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified or modified.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenyl-benzoyl, 9-fluorenylmethyl carbonate, mesylate, tosylate, triphenylmethyl (trityl), mono-methoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)-ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In some preferred embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, β-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (δ-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

The term "orthogonally protected" refers to functional groups which are protected with different classes of protecting groups, wherein each class of protecting group can be removed in any order and in the presence of all other classes (see, Barany, G., and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

The present disclosure provides compounds having reactive phosphorus groups useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^V$ state using known methods to yield, in preferred embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

In one aspect of the present disclosure, oligomeric compounds are provided having at least one non-naturally occurring internucleoside linkage. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e., a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. As used herein, the term "oligonucleoside" refers to a sequence of nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

The compounds described herein may contain one or more asymmetric centers allowing enantiomers, diastereomers, and other stereoisomeric forms that may be defined, in terms of absolute stereochemistry, as (R)— or (S)—, α or β, or as (D)- or (L)- such as for amino acids. The present disclosure is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In the context of the present disclosure, the term "oligomeric compound" refers to a polymer having at least a region that is capable of hybridizing to a nucleic acid molecule. The term "oligomeric compound" includes oligonucleotides, oligonucleotide analogs and oligonucleosides as well as mixed polymers comprising nucleic acid and non-nucleic acid components such as nucleotide mimetics, and chimeric oligomeric compounds comprising mixtures of monomeric subunits from any of these categories. Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as a peptide nucleic acid monomer. The ability to modify or substitute portions or entire monomers at each position of an oligomeric compound gives rise to a large number of possible motifs.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

As used herein, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more modified or non-naturally occurring portions. Such modified or non-naturally occurring oligonucleotides are often desired over naturally occurring forms because of desirable properties such as, for example, enhanced cellular uptake, enhanced affinity for nucleic acid target and increased stability in the presence of nucleases.

In one aspect, the present disclosure comprises a contiguous sequence of linked monomeric subunits wherein essentially each subunit has a sugar, modified sugar or sugar surrogate/mimetic portion attached to a heterocyclic base portion. The heterocyclic base (heterocyclic base moiety) can be an unmodified nucleobase or a modified nucleobase. The two most common classes of such heterocyclic bases are purines and pyrimidines. In general, any heterocyclic base capable of forming one or more hydrogen bonds with a second heterocyclic base is amenable to the present disclosure. In a preferred aspect of the present disclosure, the heterocyclic base hydrogen bonds to a complementary nucleobase present in an RNA target strand.

As used herein the term "monomer subunit" is meant to include all manner of monomer units that are amenable to oligomer synthesis with one preferred list including monomer subunits such as β-D-ribonucleosides, β-D-2'-deoxyribonucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar group has a 2'-O—CHR$_a$-4' bridging group, wherein R$_a$ is H, alkyl or substituted alkyl), other modified nucleosides, nucleoside mimetics and nucleosides having sugar surrogates.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-amino-pyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,750,692; 5,830,653; 5,763,588; 6,005,096; and 5,681,941, certain of which are commonly owned with the instant application, and each of which is herein incorporated by reference.

Oligomeric compounds of the present disclosure may also contain one or more nucleosides having modified sugar moieties. The furanosyl sugar ring can be modified in a number of ways including substitution with a substituent group (2', 3', 4' or 5'), bridging to form a BNA, substitution of the 4'-O with a heteroatom such as S or N(R) or some combination of these such as a 4'-S-2'-substituted nucleoside. Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ (2'-MOE or simply MOE) substituent group; 4'-thio modified sugars and bicyclic modified sugars (bicyclic nucleic acids).

As used herein the term "sugar surrogate" or "sugar mimetic" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

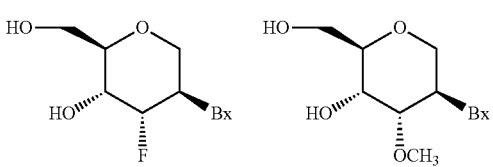

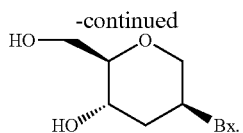

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

Each of the oligomeric compounds of the present disclosure comprises a continuous sequence of linked monomeric subunits wherein at least one of the monomeric subunits is a bicyclic nucleoside of formula I. In one aspect, each monomeric subunit that is not a bicyclic nucleoside of formula I is independently a nucleoside or a modified nucleoside (sugar modified nucleoside, base modified nucleoside, sugar and base modified nucleoside). In another aspect, each monomeric subunit that is not a bicyclic nucleoside of formula I is independently any monomeric subunit that can hybridize a nucleoside in a second or target strand, an abasic nucleoside, a nucleoside (DNA or RNA), a sugar modified nucleoside, a base modified nucleoside, a sugar and base modified nucleoside, a nucleoside mimic or a nucleoside surrogate.

The oligomeric compounds in accordance with the present disclosure can comprise from about 8 to about 80 monomeric subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomeric subunits in length or any range therewithin.

In another embodiment, the oligomeric compounds of the invention are 8 to 40 monomeric subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomeric subunits in length or any range therewithin.

In another embodiment, the oligomeric compounds of the invention are 8 to 20 monomeric subunits in length. One having ordinary skill in the art will appreciate that this embodies oligomeric compounds of 8, 9, 10, 11, 12, 13, 14, 15, 16, 17, 18, 19 or 20 monomeric subunits in length or any range therewithin.

In another embodiment, the oligomeric compounds of the invention are 12 to 23 monomeric subunits in length. One having ordinary skill in the art will appreciate that this embodies oligomeric compounds of 12, 13, 14, 15, 16, 17, 18, 19, 20, 21, 22 or 23 monomeric subunits in length or any range therewithin.

In another embodiment, the oligomeric compounds of the invention are 10 to 16 monomeric subunits in length. One having ordinary skill in the art will appreciate that this embodies oligomeric compounds of 10, 11, 12, 13, 14, 15 or 16 monomeric subunits in length or any range therewithin.

In another embodiment, the oligomeric compounds of the invention are 12 to 16 monomeric subunits in length. One having ordinary skill in the art will appreciate that this embodies oligomeric compounds of 12, 13, 14, 15 or 16 monomeric subunits in length or any range therewithin.

In another embodiment, the oligomeric compounds of the invention are 12 to 14 monomeric subunits in length. One having ordinary skill in the art will appreciate that this embodies oligomeric compounds of 12, 13, 14, 15 or 16 monomeric subunits in length or any range therewithin.

In another embodiment, the oligomeric compounds of the invention are 10 to 14 monomeric subunits in length. One having ordinary skill in the art will appreciate that this embodies oligomeric compounds of 10, 11, 12, 13 or 14 monomeric subunits in length or any range therewithin.

In certain embodiments, the present disclosure provides oligomeric compounds of any of a variety of ranges of lengths of linked monomeric subunits. In certain embodiments, the invention provides oligomeric compounds consisting of X-Y linked monomeric subunits wherein X and Y are each independently, selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X <Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-18, 11-18, 11-19, 11-20, 11-21, 11-22, 11-23, 11-24, 11-25, 11-26, 11-27, 11-28, 11-29, 11-30, 13-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomeric subunits.

More preferred ranges for the length of the oligomeric compounds in accordance with the present disclosure are 8-16, 8-40, 10-12, 10-14, 10-16, 10-18, 10-20, 10-21, 12-14, 12-16, 12-18, 12-20, 12-24, 16-21, 18-21 and 19-20 linked monomeric subunits.

In one aspect of the present disclosure, the preparation of oligomeric compounds is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—$Si(iPr)_3$ (TOM), and the 5'-O-silyl ether-T-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present disclosure.

The primary groups being used for commercial RNA synthesis are:
TBDMS=5'-O-DMT-2'-O-t-butyldimethylsilyl;
TOM=2'-O-[(triisopropylsilyl)oxy]methyl;
FPMP=5'-O-DMT-2'-O-[1(2-fluorophenyl)-4-methoxypiperidin-4-yl]; and
DOD/ACE=(5'-O-bis(trimethylsiloxy)cyclododecyloxysilyl ether-2'-O-bis(2-acetoxyethoxy)methyl.

All of the aforementioned RNA synthesis strategies are amenable to the present disclosure. Strategies that would be a hybrid of the above e.g. using a 5'-protecting group from one strategy with a 2'-O-protecting from another strategy is also amenable to the present disclosure.

As used herein, "hybridization" means pairing of complementary strands which includes pairs of oligomeric compounds or an oligomeric compound and a target nucleic acid such as a mRNA. In the present disclosure, one mechanism of pairing involves hydrogen bonding, which may be Watson-Crick, Hoogsteen or reversed Hoogsteen hydrogen bonding, between complementary heterocyclic bases. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds of the present disclosure can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present disclosure. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included in the present disclosure are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present disclosure.

The suitable target segments of the present disclosure may also be combined with their respective complementary antisense oligomeric compounds of the present disclosure to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds of the present disclosure can also be applied in the areas of drug discovery and target validation. The present disclosure comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present disclosure, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds of the present disclosure can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. The oligomeric compounds of the present disclosure, either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While the present disclosure has been described with specificity in accordance with certain of its embodiments, the following examples serve only to illustrate the invention and are not intended to limit the same.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH$_4$OAc solution. Phosphinate oligonucleotides can be prepared as described in U.S. Pat. Nos. 5,508,270.

Alkyl phosphonate oligonucleotides can be prepared as described in U.S. Pat. Nos. 4,469,863.

3'-Deoxy-3'-methylene phosphonate oligonucleotides can be prepared as described in U.S. Pat. No. 5,610,289 or U.S. Pat. No. 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Example 3

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

Example 4

Oligonucleotide Synthesis—96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

Cell Culture and Oligonucleotide Treatment

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 µL PCR cocktail (2.5× PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The room temperature reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                             (SEQ ID NO: 2)
Forward primer: AATGGCTAAGTGAAGATGACAATCAT (SEQ ID NO: 3)
Reverse primer: TGCACATATCATTACACCAGTTCGT And the PCR probe:
                                             (SEQ ID NO: 4)
FAM-TTGCAGCAATTCACTGTAAAGCTGGAAAGG-TAMRA,
``` where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).
Example 13
Preparation of Compound 15
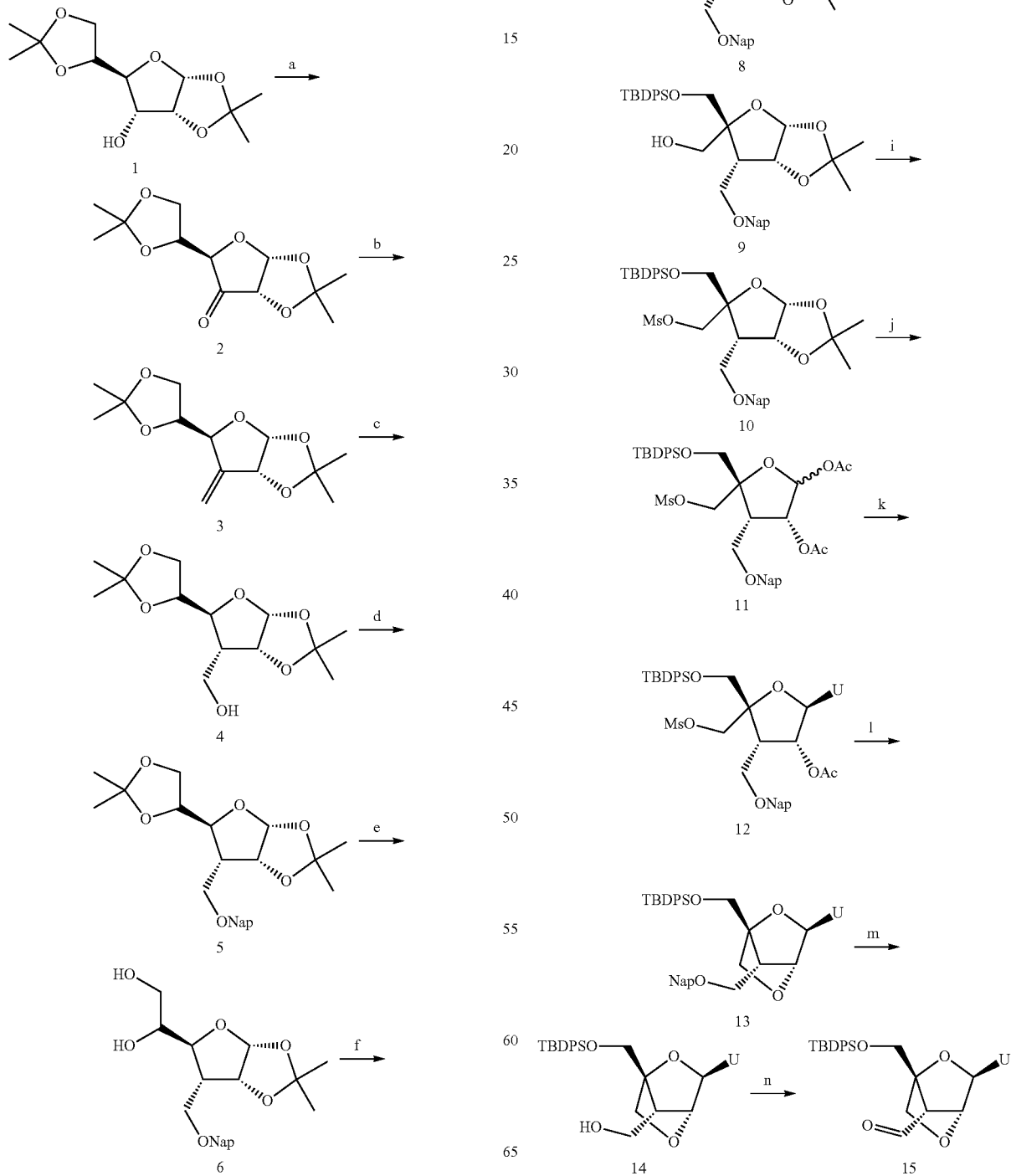

-continued (a) oxalyl chloride, DMSO, Et$_3$N, CH$_2$Cl$_2$
(b) PPH$_3$CH$_3$Br, nBuLi, THF, 82% from 1
(c) 9-BBN, THF then NaBO$_3$, EtOH/water, 93%
(d) NaH, NapBr, THF, 86%
(e) CH$_3$CO$_2$H, H$_2$O
(f) NaIO$_4$, dioxane, water
(g) NaOH, HCHO, THF, 55% from 5
(h) TBDPSCl, Et$_3$N, CH$_2$Cl$_2$, 58%
(i) MsCl, Et$_3$N, DMAP, CH$_2$Cl$_2$
(j) AcOH, Ac$_2$O, catalytic H$_2$SO$_4$
(k) N,O-BSA, TMSOTf, CH$_3$CN
(l) K$_2$CO$_3$, MeOH, 54% from 9
(m) DDQ, CH$_2$Cl$_2$, H$_2$O, 90%
(n) Dess-Martin Periodinane, CH$_2$Cl$_2$ A) Preparation of Compound 3

Dimethylsulfoxide (2.12 mL, 30.0 mmol) was added dropwise to a cold (−78° C.) solution of oxalyl chloride (1.32 mL, 15.0 mmol) in CH$_2$Cl$_2$ (60 mL). After stirring for 30 min, a solution of commercially available 1,2:5,6-Di-O-isopropylidene-α-D-allofuranose (2.60 g, 10.0 mmol, commercially available from Pfanstiehl Laboratories, Inc.; order # D-126), Compound 1, in CH$_2$Cl$_2$ (20 mL) was added to the reaction. The stirring was continued for 45 min at −78° C. and triethylamine (6.30 mL, 45.0 mmol) was added to the reaction. The reaction was stirred at −78° C. for 15 min after which the ice bath was removed and the reaction was allowed to gradually warm over 45 min. The reaction was then poured into CH$_2$Cl$_2$ and the organic phase was sequentially washed with 5% aqueous HCl, saturated NaHCO$_3$, brine, dried (Na$_2$SO$_4$) and concentrated under vacuum to provide ketone, Compound 2, which was used without further purification.

nBuLi (2.5 M, 6.0 mL, 15.0 mmol) was added dropwise to a cold (0° C.) stirring solution of triphenylphosphonium bromide (5.35 g, 15.0 mmol) in dry THF (80 mL). After stirring for 1 hour, the red solution was cooled to −50° C. and a solution of ketone, Compound 2 from above (10.0 mmol) in dry THF (20 mL) was added dropwise to the reaction. The reaction was gradually allowed to warm to room temperature and the stirring was continued for another 16 hours. The reaction was diluted with diethyl ether (60 mL) and the resulting suspension was filtered through celite. The filtrate was diluted with ether and the organic layer was sequentially washed with water and brine then dried (Na$_2$SO$_4$) and concentrated. Purification by column chromatography (SiO$_2$, eluting with 10 to 20% EtOAc in hexanes) provided olefin, Compound 3 (2.09 g, 82% from Compound 1) as a colorless oil.

B) Preparation of Compound 4

9-BBN (0.5 M in THF, 47.0 mL, 23.5 mmol) was added to olefin, Compound 3 (1.99 g, 7.8 mmol) and the resulting solution was stirred at room temperature for 16 hours. A suspension of NaBO$_3$.4H$_2$O (6.79 g, 44.7 mmol) in ethanol/water (1:1, 96 mL) was added to the reaction and the whole was stirred vigorously at 55° C. for 4 hours. The reaction was then cooled in an ice bath and carefully neutralized using glacial acetic acid (pH ~8) and the solvent was evaporated under vacuum. The residue was dissolved in EtOAc and the organic layer was washed with brine, dried and concentrated. Purification by column chromatography (SiO$_2$, eluting with 25 to 30% EtOAc in hexanes) provided alcohol, Compound 4 (2.00 g, 93% from Compound 1) as a colorless oil.

C) Preparation of Compound 5

Sodium hydride (0.44 g, 10.9 mmol) was added carefully to a cold (0° C.) solution of alcohol, Compound 4 (2.0 g, 7.3 mmol) and naphthyl bromide (2.40 g, 10.9 mmol) in DMF (7.3 mL). The reaction was gradually warmed to room temperature and stirred for 16 hours after which the reaction was quenched with water. The reaction was diluted with EtOAc and the organic layer was washed with water, brine, dried and concentrated. Purification by column chromatography (SiO$_2$, 10% to 20% EtOAc in hexanes) provided alcohol, Compound 5 (2.58 g, 86%) and unreacted starting alcohol, Compound 4 (0.25 g, 13%).

D) Preparation of Compound 8

Compound 5 (2.57 g, 6.2 mmol) was dissolved in glacial acetic acid (25 mL) and H$_2$O (10 mL). The reaction was stirred at room temperature for 16 h after then concentrated under vacuum. The residue was dissolved in EtOAc and the organic layer was washed with saturated NaHCO$_3$, brine, dried and concentrated to provide Compound 6, which was used without further purification.

A solution of sodium periodate (1.32 g, 6.2 mmol) in water (36 mL) was added to a solution of the crude Compound 6 in 1,4-dioxane (18 mL). After stirring at room temperature for 90 minutes, the reaction was extracted with EtOAc, The organic layer was further washed with water and brine then dried (Na$_2$SO$_4$) and concentrated to provide Compound 7, which was used without further purification.

The crude Compound 7 was dissolved in a mixture of THF:H$_2$O (1:1, 12 mL) and the reaction was cooled in an ice bath. Formaldehyde (3.0 mL, 35% w/w) and 2 N NaOH (8 mL) were added to the reaction. After stirring at room temperature for 16 h, additional THF (10 mL) and formaldehyde (1.5 mL) was added to the reaction and the stirring was continued for an additional 5 days at 35° C. The reaction was partitioned between EtOAc and water and the organic layer was washed with additional 1 N NaOH, water, brine, dried and concentrated. Purification by column chromatography (SiO$_2$, eluting with 50 to 90% EtOAc in hexanes) provided Compound 8 (1.26 g, 55% from Compound 5) as a colorless oil.

E) Preparation of Compound 9 tert-Butyldiphenylsilyl chloride (1.10 mL, 4.3 mmol) was added to a cold (0° C.) solution of Compound 8 (1.25 g, 3.4 mmol) and triethylamine (0.61 mL, 4.3 mmol) in dichloromethane (22 mL). After stirring at room temperature for 16 hours, methanol (1 mL) was added to the reaction. After stirring for 1 hour, the reaction was diluted with EtOAc and sequentially washed with 5% HCl, saturated NaHCO$_3$, brine, dried (Na$_2$SO$_4$) and concentrated. Purification by column chromatography (SiO$_2$, eluting with 10% to 40% EtOAc/hexanes) provided Compound 9 (1.16 g, 58%) as an oil (0.81 g of the regioisomeric silyl protected diol was also isolated).

F) Preparation of Compound 13

Methanesulfonyl chloride (0.22 mL, 2.8 mmol) was added to a cold (0° C.) solution of Compound 9 (1.16 g, 1.9 mmol), diisopropylethylamine (0.5 mL, 2.8 mmol) and 4-dimethylaminopyridine (35 mg, 0.3 mmol) in CH$_2$Cl$_2$ (10 mL). After stirring at room temperature for 1 hour, the reaction was diluted with chloroform and the organic layer was sequentially washed with 5% aqueous HCl, saturated NaHCO$_3$ and brine. The washed organic phase was dried (Na$_2$SO$_4$) and concentrated under vacuum to provide Compound 10, which was used without any purification.

Concentrated H$_2$SO$_4$ (2 drops) was added to a solution of Compound 10 (from above) in glacial acetic acid (6.0 mL) and acetic anhydride (1.2 mL). After stirring at room temperature for 1 hour, the reaction was poured into EtOAc and the organic layer was washed with water, saturated NaHCO$_3$, brine, dried (Na$_2$SO$_4$) and concentrated under vacuum to provide Compound 11, which was used without further purification.

N,O-Bis(trimethylsilyl)acetamide (2.80 mL, 11.3 mmol) was added to a suspension of crude Compound 11 (from above) and uracil (0.42 g, 3.8 mmol) in CH$_3$CN (10 mL). After heating at 40° C. for 15 min a clear solution was obtained that was cooled in an ice bath to which trimethylsilyl triflate (0.68 mL, 3.8 mmol) was added. The reaction mixture was heated to reflux for 2 hours, cooled to room temperature and poured into EtOAc. The organic layer was washed with saturated NaHCO$_3$ and brine then dried (Na$_2$SO$_4$). The washed organic phase was concentrated under vacuum to provide crude nucleoside, Compound 12, which was used without purification.

K$_2$CO$_3$ (0.55 g, 4.0 mmol) was added to a solution of nucleoside, Compound 12 (from above) in MeOH (20 mL). After stirring at room temperature for 16 h, the reaction was neutralized with glacial acetic acid and concentrated under vacuum. The residue was partitioned between EtOAc and water and the organic layer was washed with brine, dried (Na$_2$SO$_4$) and concentrated under vacuum. Purification by column chromatography (SiO$_2$, eluting with 10 to 15% acetone in chloroform) provided nucleoside, Compound 13 (0.66 g, 54% from Compound 9) as a white solid.

G) Preparation of Compound 14

2,3-Dichloro-5,6-dicyano-1,4-benzoquinone (DDQ) (0.34 g, 1.5 mmol) was added to a solution of nucleoside, Compound 13 (0.66 g, 1.0 mmol) in dichloromethane (10 mL) and H$_2$O (0.05 mL). After stirring for 3 h at room temperature, the reaction was concentrated under vacuum and the residue was dissolved in EtOAc. The organic layer was sequentially washed with water, 10% NaHSO$_3$, saturated NaHCO$_3$, brine, dried (Na$_2$SO$_4$) and concentrated. Purification by column chromatography (SiO$_2$, 33% acetone in chloroform) provided nucleoside, Compound 14 (0.47 g, 90%) as a white solid.

H) Preparation of Compound 15

Dess-Martin periodinane (0.41 g, 1.0 mmol) was added to a solution of nucleoside, Compound 14 (0.41 g, 0.81 mmol) in dichloromethane (8 mL). After stirring at room temperature for 2 hours, TLC analysis indicated no starting material, Compound 14, a solution of 10% sodium thiosulfate and saturated NaHCO$_3$ (1:1, 4 mL) was added and the biphasic mixture was stirred vigorously for 30 minutes. The reaction was diluted with chloroform and the organic layer was washed with brine, dried (Na$_2$SO$_4$) and concentrated to provide crude Compound 15, which was used without further purification.

Example 14

Preparation of 3-O-Naphthylmethyl-4-(hydroxymethyl)-1,2-O-isopropylidene-α-D-erythropentofuranose (Compound 16)

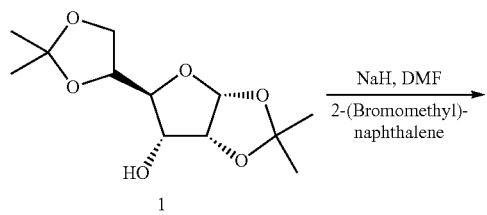

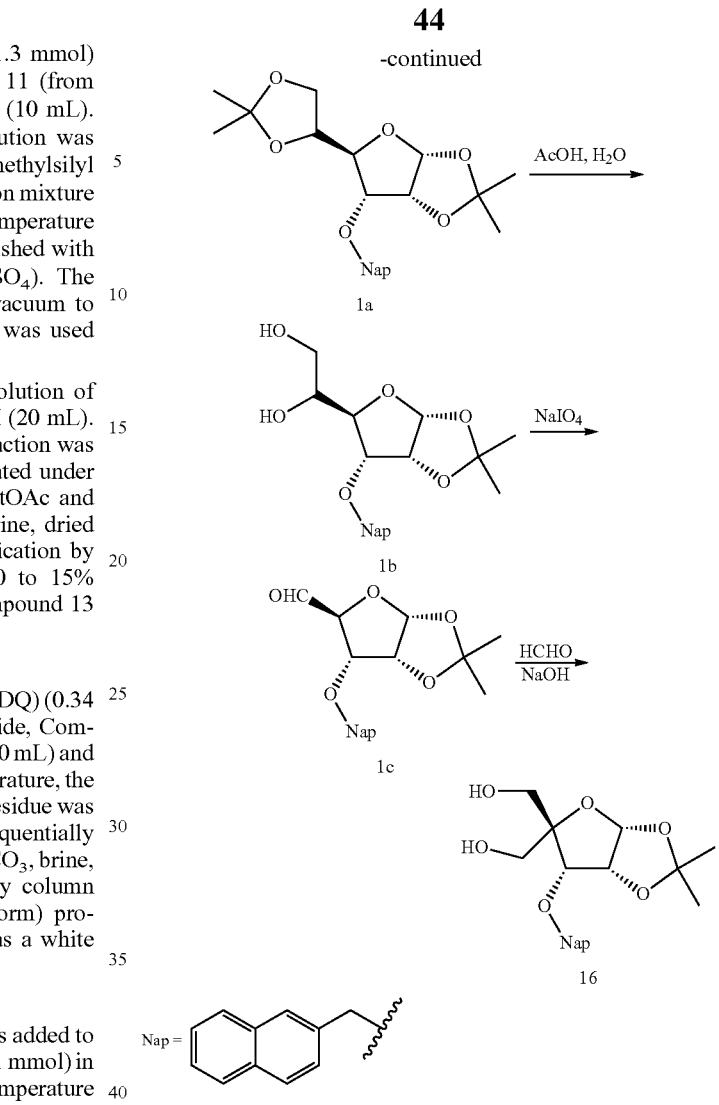

A) Preparation of Compound 1a 1,2:5,6-Di-O-isopropylidene-α-D-allofuranose (135 g, 519.0 mmol, commercially available from Pfanstiehl Laboratories, Inc.; order # D-126), Compound 1, and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed that the starting sugar, Compound 1, had been consumed. The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over P$_2$O$_5$ for 16 hours to provide Compound 1a (206.0 g, 99%) as an off-white solid. $^1$H NMR (300 MHz, CDCl$_3$) d 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1), 4.15 (m, 1H), 4.03-3.86 (m, 3H), 1.61 (s, 3H), 1.36 (s, 9H).

B) Preparation of Compound 1b

Compound 1a (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 1a. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with a saturated solution of sodium bicarbonate then brine, dried ($Na_2SO_4$), filtered and concentrated under reduced pressure to provide 1b as a yellow foam, which was used without further purification.

C) Preparation of Compound 1c

A solution of $NaIO_4$ (107.0 g) in water (3 L) was added over 40 minutes to a stirred (mechanical stirrer) solution of crude compound 1b in dioxane (1.5 L). After 60 minutes the reaction mixture was poured into EtOAc (1.5 L) and the organic layer was separated, washed with water (1 L) and brine (1 L) then dried ($Na_2SO_4$) and concentrated to provide Compound 1c as a yellow oil, which was used without further purification.

D) Preparation of Compound 16

Compound 1c was dissolved in a mixture of THF (500 mL) and water (500 mL) and the reaction was cooled in an ice bath. 2 N NaOH (600 mL) and formaldehyde (250 mL of a 37% aqueous solution) were added to the reaction with stirring continued at room temperature for 3 days. The reaction was then poured into EtOAc (1 L) and washed with water (1 L), brine (1 L) and evaporated under reduced pressure to a volume of approximately 200 mL with a white precipitate formed during the evaporation process. Hexanes (300 mL) was added to the precipitate and the mixture was allowed to stand for 16 hours after which the white solid was collected by filtration, washed with hexanes and dried under high vacuum over $P_2O_5$ to provide Compound 16 as a white solid (124 g, 66% from Compound 1a). $^1$H NMR (300 MHz, $CDCl_3$) d 7.85 (m, 4H), 7.48 (m, 3H), 5.75 (d, 1H, J=3.9), 4.96 (d, 1H, J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

Example 15

Preparation of Compound 24

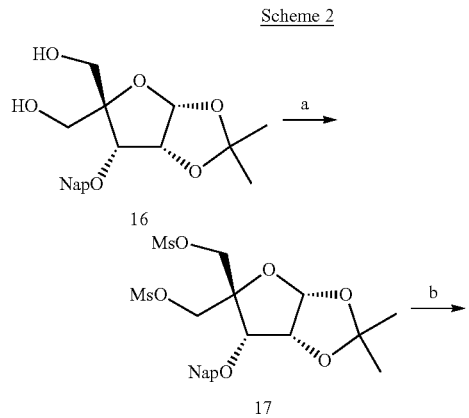

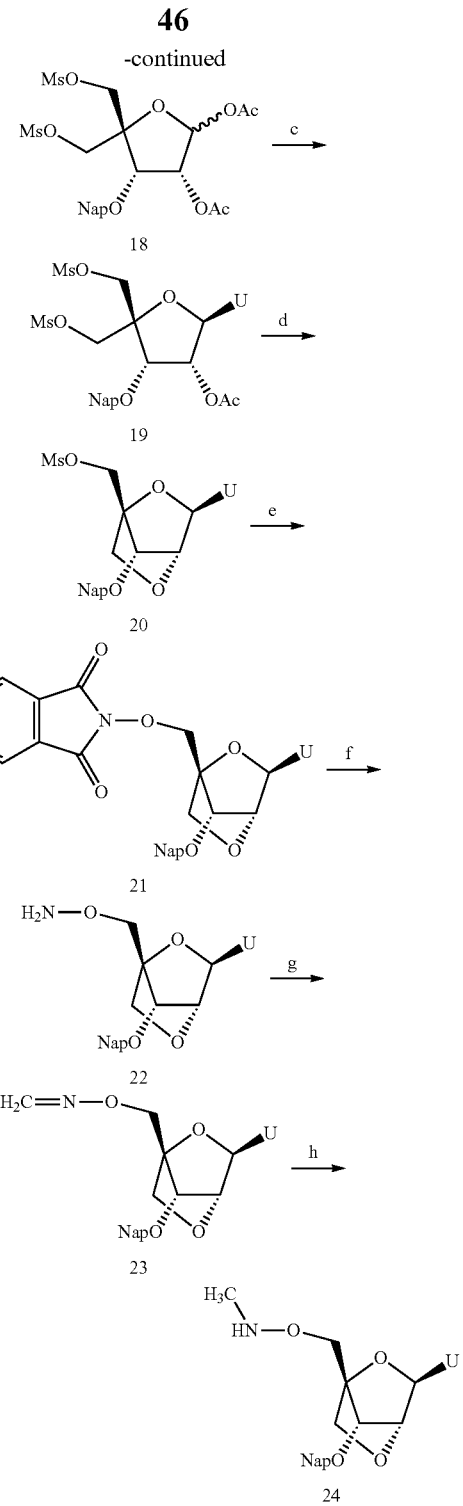

(a) MsCl, DMAP, $Et_3N$, $CH_2Cl_2$
(b) AcOH, $Ac_2O$, catalytic $H_2SO_4$
(c) N,O-BSA, TMSOTf, $CH_3CN$,
(d) $K_2CO_3$, MeOH
(e) N-hydroxythalimide, DBU, MeCN
(f) Hydrazine, EtOH, dioxane
(g) HCHO, MeOH, 36% from 16
(h) $NaBH_3CN$, AcOH

A) Preparation of Compound 17

Methanesulfonyl chloride (6.6 mL, 83.3 mmol) was added dropwise to a cold (0° C.) solution of Compound 16 (12.0 g, 33.3 mmol) DIPEA (14.5 mL, 83.3 mmol) and dimethylaminopyridine (1.0 g, 8.3 mmol) in dichloromethane (100 mL). After stirring for 3 hours, the reaction was diluted with chloroform and the organic layer was sequentially washed with 5% HCl, saturated NaHCO$_3$ and brine then dried (Na$_2$SO$_4$) and concentrated. Purification by column chromatography (SiO$_2$, eluting with 40 to 50% EtOAc in hexanes) provided Compound 17 (15.12 g, 88%) as a white solid.

B) Preparation of Compound 23

Concentrated sulfuric acid (5 to 10 drops) was added to a solution of Compound 17 (15.1 g, 29.3 mmol) and acetic anhydride (20 mL) in glacial acetic acid (90 mL). After stirring for 2 hours at room temperature, the reaction was concentrated under high vacuum and the residue was diluted with EtOAc. The organic layer was washed with saturated NaHCO$_3$ (until aqueous layer pH>10) and brine then dried (Na$_2$SO$_4$) and concentrated to provide Compound 18, which was used without further purification.

N,O-Bis(trimethylsilyl)acetamide (8.37 mL, 77.0 mmol) was added to a suspension of crude diacetate, Compound 18 (from above) and uracil (6.89 g, 61.6 mmol) in CH$_3$CN (150 mL). After heating at 40° C. for 15 min to get a clear solution, the reaction was cooled in an ice bath and trimethylsilyl triflate (8.37 mL, 46.2 mmol) was added. After refluxing for 2 hours, the reaction was cooled to room temperature and poured into EtOAc. The organic layer was washed with saturated NaHCO$_3$ and brine then dried (Na$_2$SO$_4$) and concentrated under vacuum to provide crude Compound 19, which was used without purification.

K$_2$CO$_3$ (8.28 g, 60.0 mmol) was added to a solution of Compound 19 (from above) in MeOH (300 mL). After stirring at room temperature for 16 h, the reaction was neutralized with glacial acetic acid and concentrated under vacuum. The residue was partitioned between EtOAc and water and the organic layer was washed with brine, dried (Na$_2$SO$_4$) and concentrated under vacuum to provide Compound 20, which was used without further purification.

DBU (8.37 mL, 56.0 mmol) was added to a solution of crude Compound 20 (13.25 g, 28.0 mmol) and N-hydroxythalimide (9.11 g, 56.0 mmol) in acetonitrile (60 mL). The deep red solution was warmed to 50° C. and stirred for 14 hours, after which it was neutralized with 10% HCl. The reaction was partitioned between EtOAc and water and the organic layer was washed with saturated NaHCO$_3$ and brine then dried (Na$_2$SO$_4$) and concentrated to provide Compound 21, which was used without further purification.

Hydrazine (1.80 mL, 37.0 mmol) was added to a solution of crude Compound 21 (from above) in ethanol/dioxane (1:1, 180 mL). After stirring for 2 hours at room temperature, the white solid that was formed was filtered and the filtrate was concentrated to provide a yellowish solid. The solid was dissolved in methanol and slurried with silica gel. The slurry was poured onto a plug of silica gel and eluted (15 to 20% MeOH/CHCl$_3$). The fractions containing product, Compound 22, were pooled together and concentrated to provide partially pure Compound 22 as a yellowish solid, which was used without further purification.

Formaldehyde (1.50 mL of a 30% solution) was added to a solution of crude Compound 22 in methanol (100 mL). After stirring for 2 hours at room temperature, the solvent was evaporated under vacuum and the residue was adsorbed onto silica gel and filtered through a plug of silica gel (eluting with 10% methanol in chloroform). The fractions containing the product were pooled and concentrated to provide partially pure, Compound 23, which was purified (SiO$_2$, 2% methanol in chloroform), followed by another purification (90% EtOAc in hexanes) to provide Compound 23 (4.46 g, still slightly impure, 36% from Compound 16) as a white foam.

C) Preparation of Compound 24

Sodium cyanoborohydride (2 mg) was added to a cold (0° C.) solution of Compound 23 in glacial acetic acid. After stirring for 1 hour, the reaction was diluted with EtOAc and the organic layer was washed with saturated NaHCO$_3$, brine, dried (Na$_2$SO$_4$) and concentrated to provide Compound 24, which was used without further purification. LCMS: retention time 2.73 min; calculated M+H, 426.16. found 426.1.

Example 16

Preparation of Compound 29

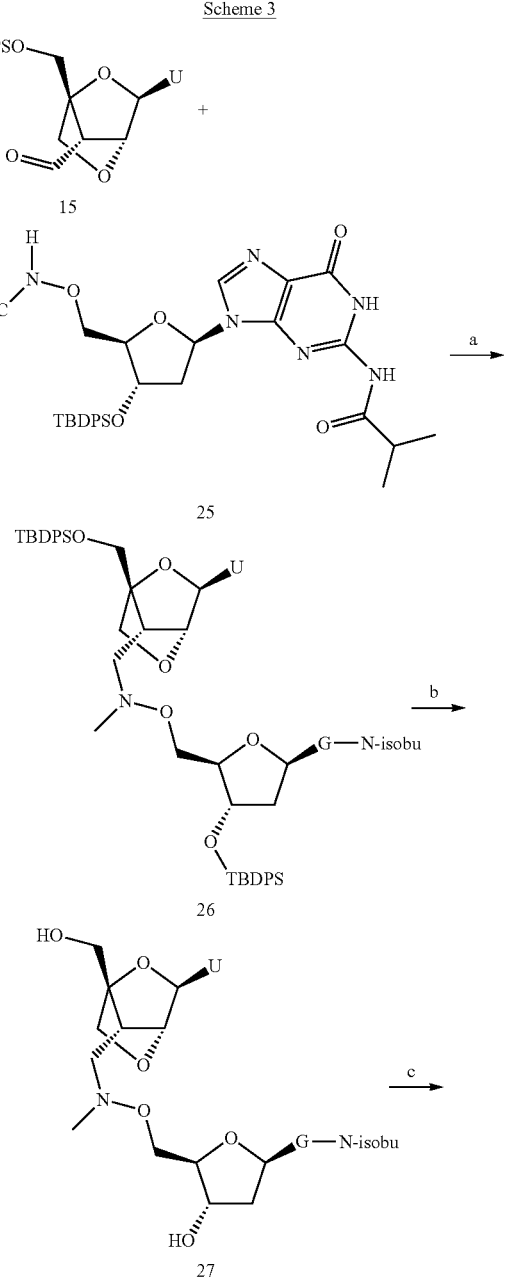

Scheme 3

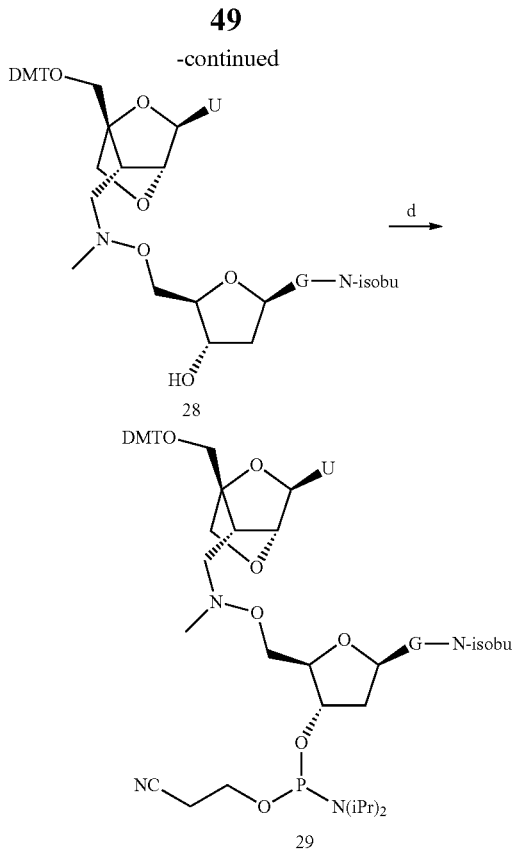

(a) PPTS, 8M BH₃/pyridine, MeOH, 93%
(b) Et₃N•3HF, Et₃N, THF, 97%
(c) DMTCl, pyridine, 65%
(d) (iPr₂N)₂POCH₂CH₂CN, tetrazole, NMI, DMF, 84%

A) Preparation of Compound 26

Compound 25 (0.79 mmol) was prepared as described by Perbost et al (*J. Org. Chem.* 1995, 60, 5150). After preparation Compound 25 was immediately mixed with Compound 15 (0.81 mmol, in 4 mL methanol, 0.2 g of PPTS and 0.1 mL of 8 M BH₃/pyridine) resulting in conversion to the dimer, Compound 26, using the procedure described by Swayze et al. (*Synlett,* 1997, 859). After stirring at room temperature for 4 hours, the reaction was diluted with EtOAc and the organic layer was washed with saturated NaHCO₃ and brine then dried (Na₂SO₄) and concentrated. Purification by column chromatography (SiO₂, eluting with 2 to 5% methanol in chloroform) yielded dimer, Compound 26 (0.80 g, 93%)

B) Preparation of Compound 27

Triethylamine trihydrofluoride (1.78 mL, 11.0 mmol) was added to a solution of dimer, Compound 26 (0.80 g, 0.73 mmol) and triethylamine (0.51 g, 3.7 mmol) in THF (11 mL). After stirring for 16 hours at room temperature, the reaction was concentrated under vacuum and the residue was purified by column chromatography (SiO₂, eluting with chloroform to 15% methanol in chloroform) to provide dimer, Compound 27 (0.44 g, 97%).

C) Preparation of Compound 28

Dimethoxytrityl chloride (0.26 g, 0.78 mmol) was added to a solution of dimer, Compound 27 (0.44 g, 0.71 mmol) in pyridine (3.5 mL). After stirring for 16 hours at room temperature, the reaction was diluted with EtOAc and the organic layer was washed with saturated NaHCO₃, brine, dried (Na₂SO₄) and concentrated. Purification by column chromatography (SiO₂, eluting with chloroform to 10% methanol in chloroform) provided dimer, Compound 28 (0.42 g, 65%) and unreacted starting material dimer, Compound 27 (0.11 g, 24%).

D) Preparation of Compound 29

2-Cyanoethyl tetraisopropylphosphorodiamidite (0.18 mL, 0.58 mmol) was added to a solution of dimer, Compound 28 (0.42 g, 0.46 mmol), tetrazole (21 mg, 0.3 mmol) and N-methylimidazole (8 µL, 0.1 mmol) in DMF (2 mL). After stirring at room temperature for 8 h, the reaction was poured into EtOAc and the organic layer was washed with 90% brine then dried (Na₂SO₄) and concentrated. Purification by column chromatography (SiO₂, eluting with 8% methanol, 0.5% triethylamine in chloroform) provided phosphoramidite 29 as a white solid. Amidite, Compound 29 was dissolved in minimum volume of EtOAc and this solution was added to a rapidly stirring solution of hexanes. The resulting precipitate was collected and dried over high vacuum to yield pure amidite 29 (0.42 g, 84%) as a white solid. $^{31}$P NMR (CDCl₃) δ: 149.36, 148.42.

Example 17

Preparation of Compound 34

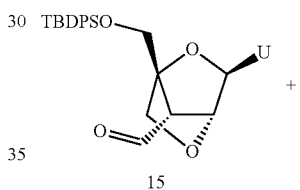

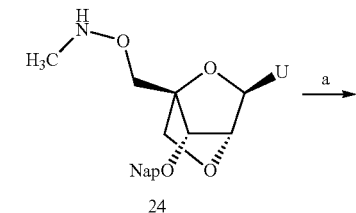

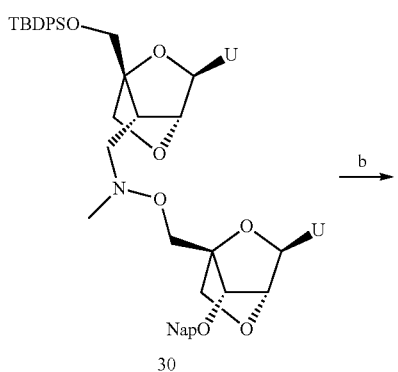

-continued
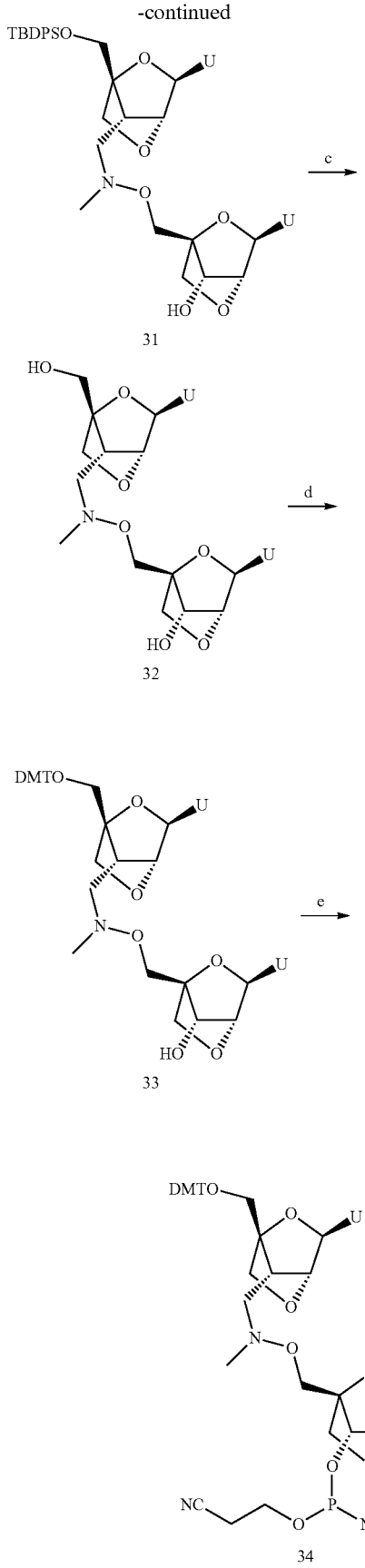
Compound 34 is prepared from Compound 24 and Compound 15 as per the procedures illustrated in Example 16.
Example 18
General Procedures for the Preparation of Compound 43a
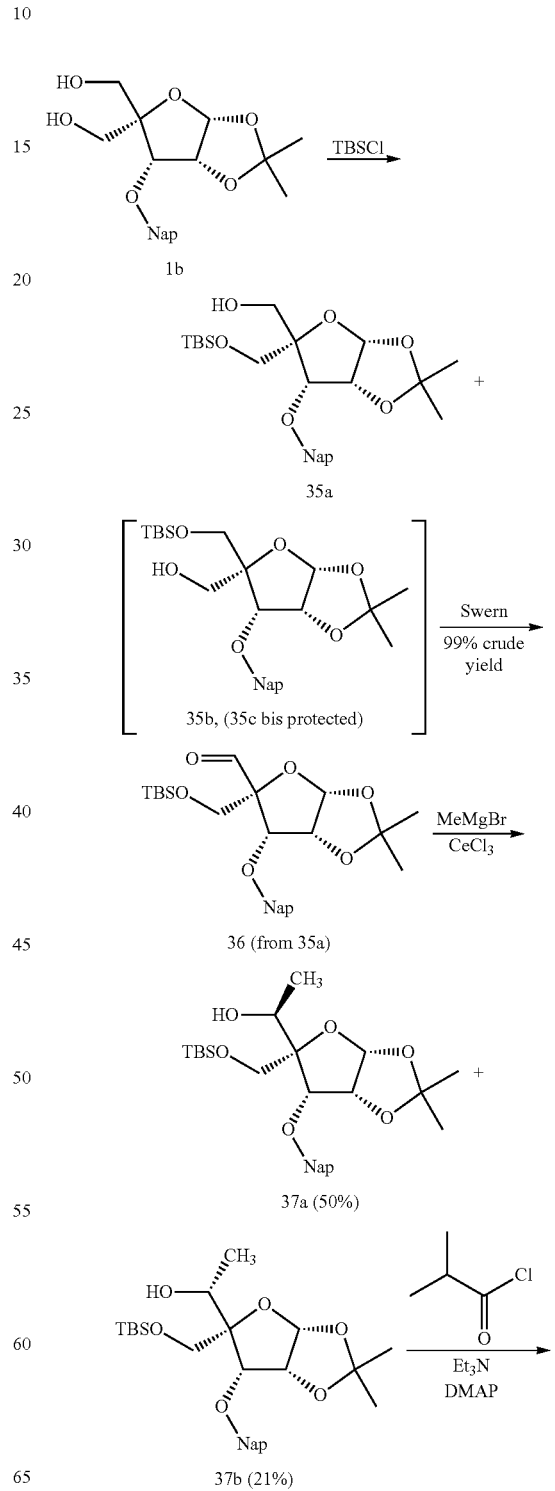

-continued
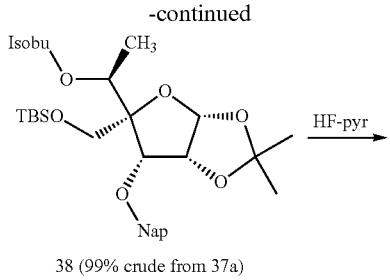
38 (99% crude from 37a)
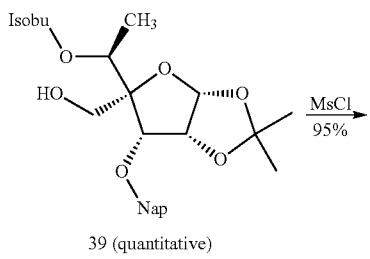
39 (quantitative)
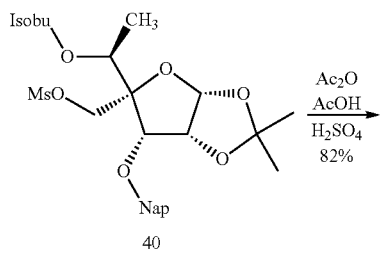
40
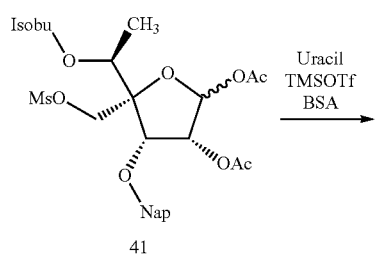
41
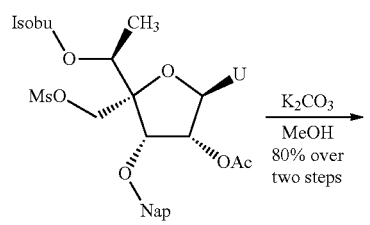
42
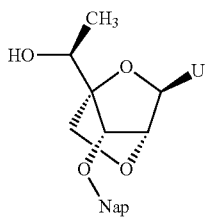
43a
The 5'-(S)-isomer Compound 43a is shown but the 5'-(R)-isomer Compound 43b or the racemic mixture Compound 43 can also be prepared using Compound 35b or a mixture of 35a and 35b instead of 35a.
Example 19
Preparation of Compound 53
Scheme 5
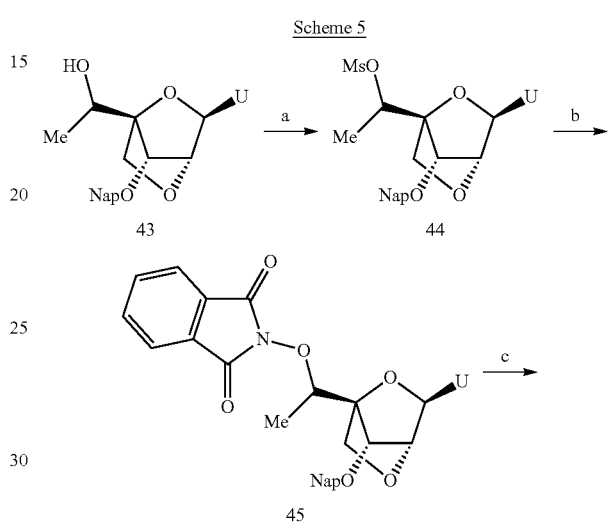
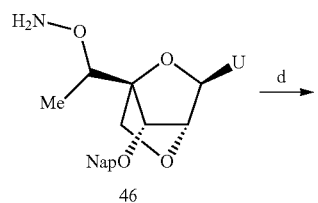
46
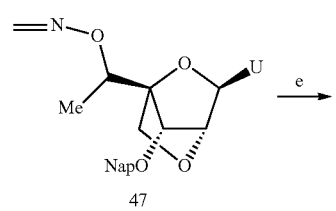
47
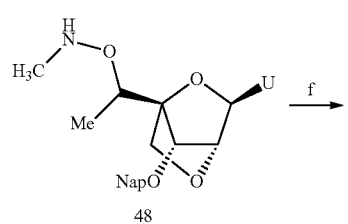
48

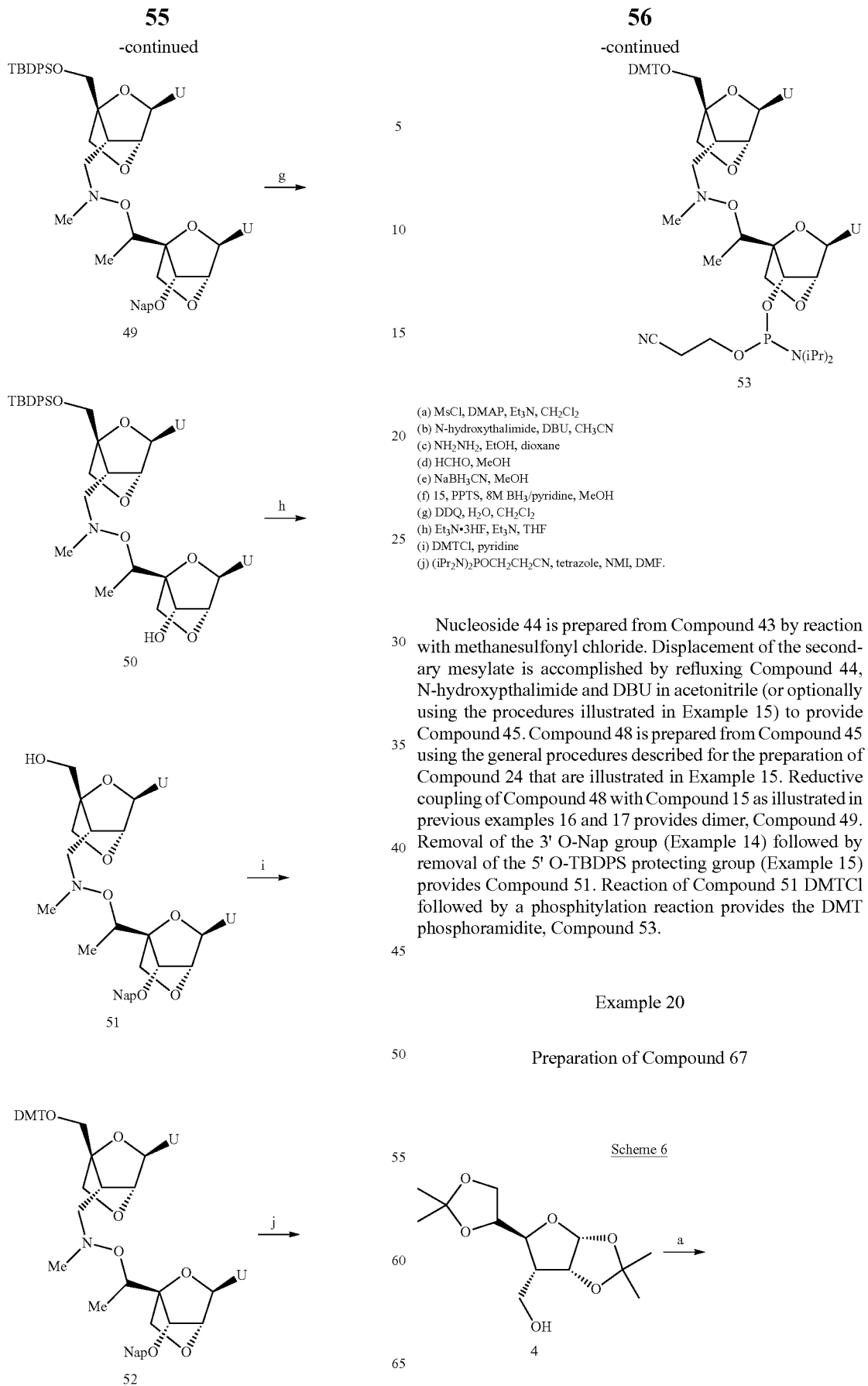

(a) MsCl, DMAP, Et₃N, CH₂Cl₂
(b) N-hydroxythalimide, DBU, CH₃CN
(c) NH₂NH₂, EtOH, dioxane
(d) HCHO, MeOH
(e) NaBH₃CN, MeOH
(f) 15, PPTS, 8M BH₃/pyridine, MeOH
(g) DDQ, H₂O, CH₂Cl₂
(h) Et₃N•3HF, Et₃N, THF
(i) DMTCl, pyridine
(j) (iPr₂N)₂POCH₂CH₂CN, tetrazole, NMI, DMF.

Nucleoside 44 is prepared from Compound 43 by reaction with methanesulfonyl chloride. Displacement of the secondary mesylate is accomplished by refluxing Compound 44, N-hydroxypthalimide and DBU in acetonitrile (or optionally using the procedures illustrated in Example 15) to provide Compound 45. Compound 48 is prepared from Compound 45 using the general procedures described for the preparation of Compound 24 that are illustrated in Example 15. Reductive coupling of Compound 48 with Compound 15 as illustrated in previous examples 16 and 17 provides dimer, Compound 49. Removal of the 3' O-Nap group (Example 14) followed by removal of the 5' O-TBDPS protecting group (Example 15) provides Compound 51. Reaction of Compound 51 DMTCl followed by a phosphitylation reaction provides the DMT phosphoramidite, Compound 53.

Example 20

Preparation of Compound 67

Scheme 6

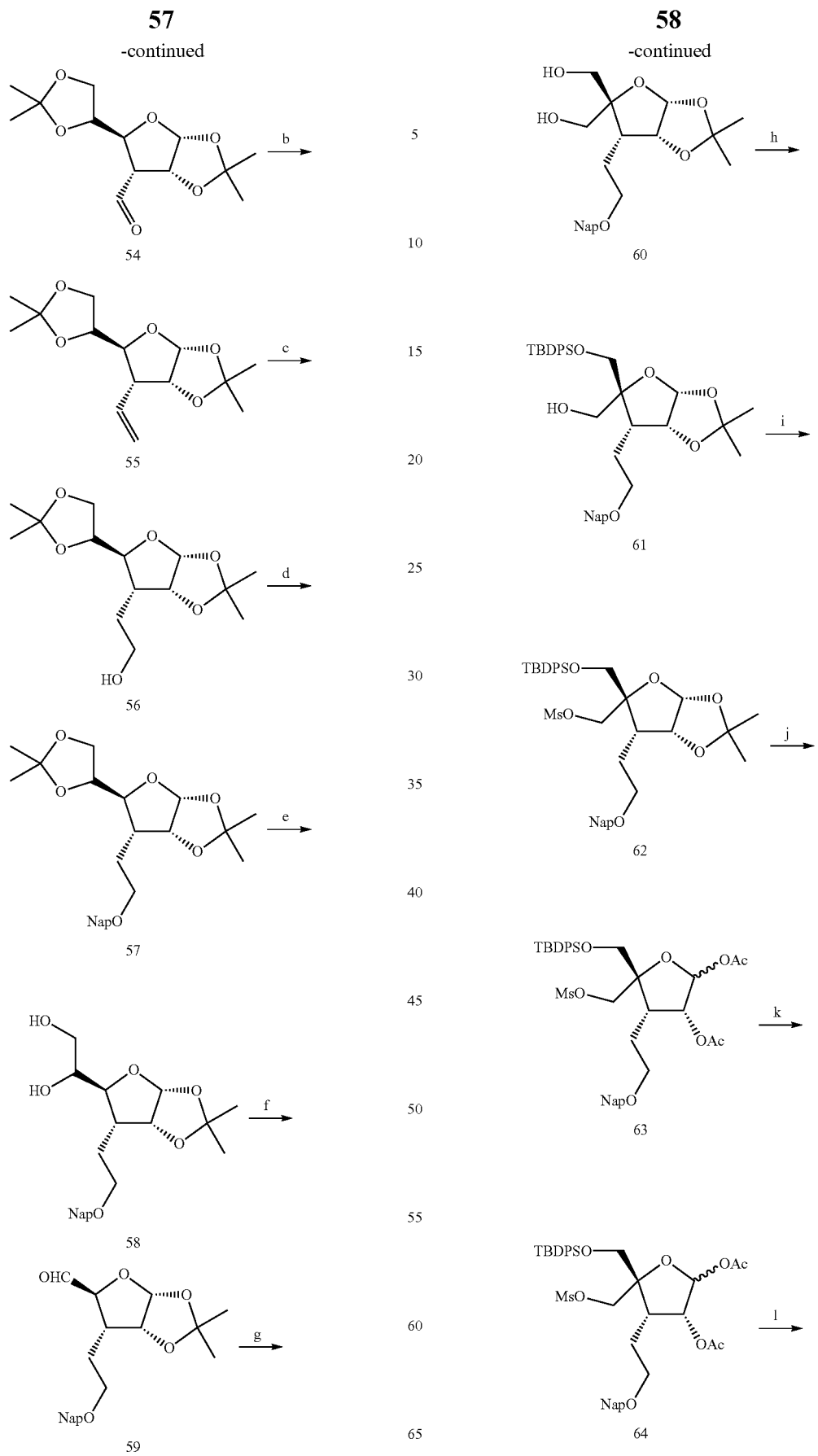

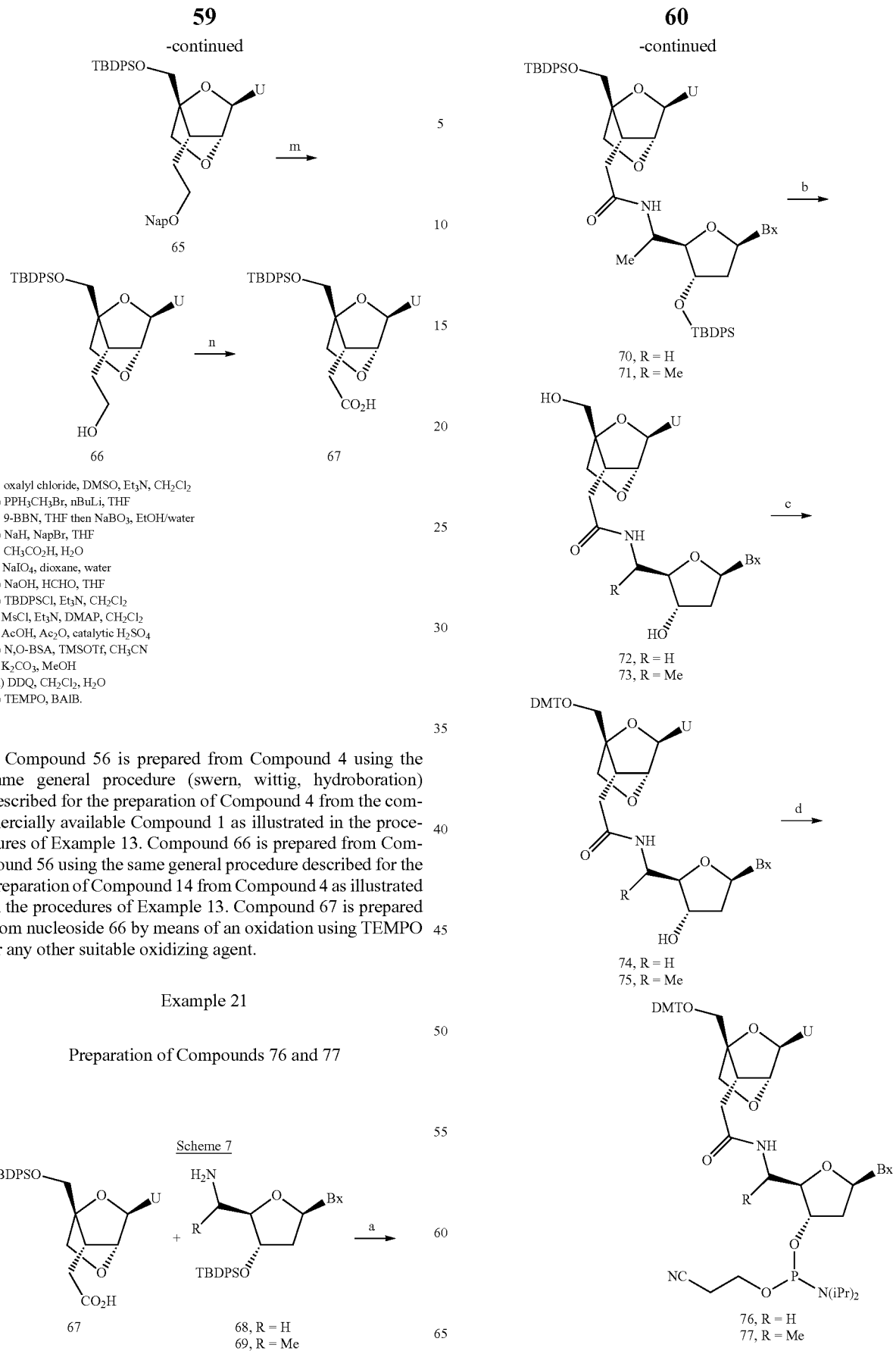

(a) oxalyl chloride, DMSO, Et₃N, CH₂Cl₂
(b) PPH₃CH₃Br, nBuLi, THF
(c) 9-BBN, THF then NaBO₃, EtOH/water
(d) NaH, NapBr, THF
(e) CH₃CO₂H, H₂O
(f) NaIO₄, dioxane, water
(g) NaOH, HCHO, THF
(h) TBDPSCl, Et₃N, CH₂Cl₂
(i) MsCl, Et₃N, DMAP, CH₂Cl₂
(j) AcOH, Ac₂O, catalytic H₂SO₄
(k) N,O-BSA, TMSOTf, CH₃CN
(l) K₂CO₃, MeOH
(m) DDQ, CH₂Cl₂, H₂O
(n) TEMPO, BAIB.

Compound 56 is prepared from Compound 4 using the same general procedure (swern, wittig, hydroboration) described for the preparation of Compound 4 from the commercially available Compound 1 as illustrated in the procedures of Example 13. Compound 66 is prepared from Compound 56 using the same general procedure described for the preparation of Compound 14 from Compound 4 as illustrated in the procedures of Example 13. Compound 67 is prepared from nucleoside 66 by means of an oxidation using TEMPO or any other suitable oxidizing agent.

Example 21

Preparation of Compounds 76 and 77

Scheme 7

(a) HATU, DIPEA, DMF
(b) Et$_3$N•3HF, Et$_3$N, THF
(c) DMTCl, pyridine
(d) (iPr$_2$N)$_2$POCH$_2$CH$_2$CN, tetrazole, NMI, DMF.

Amide dimers, compounds 70 and 71 are prepared by coupling the amines, compounds 68 and 69 (made as per: De Mesmaeker et al in *Synlett,* 1997, 1287 and references cited therein) with acid, Compound 67 using HATU and DIPEA in DMF or any other suitable peptide coupling procedure. The DMT phosphoramidites, compounds 76 and 77 are prepared from amide dimers, compounds 70 and 71, using the general procedures illustrated in Example 16.

Example 22

Preparation of Compounds 84 and 85

Scheme 8

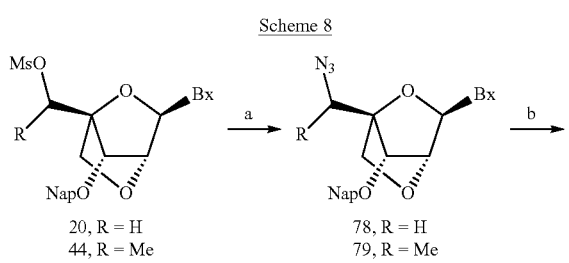

20, R = H
44, R = Me

78, R = H
79, R = Me

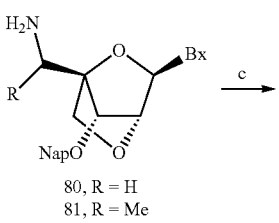

80, R = H
81, R = Me

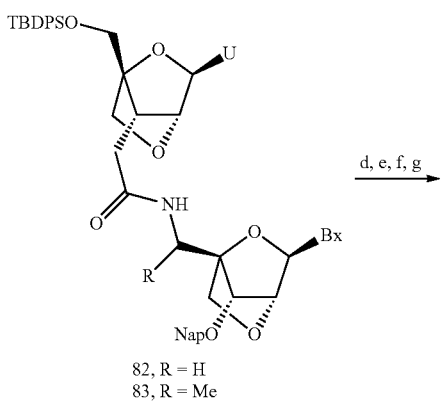

82, R = H
83, R = Me

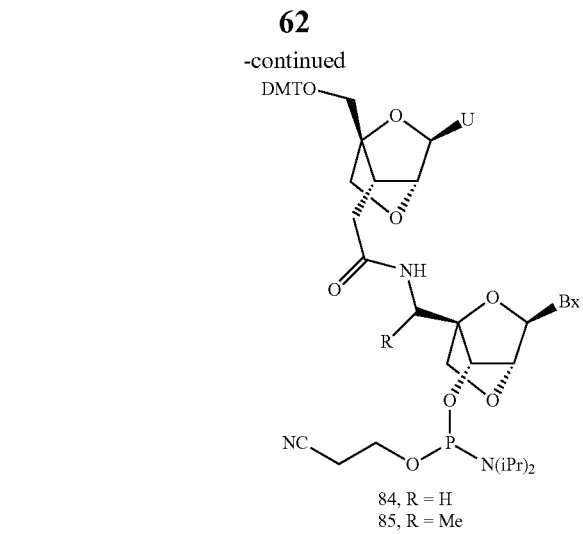

84, R = H
85, R = Me (a) NaN$_3$, DMF
(b) nBu$_3$P, MeOH
(c) 61, HATU, DIPEA, DMF
(d) DDQ, CH$_2$Cl$_2$, H$_2$O
(e) Et$_3$N•3HF, Et$_3$N, THF
(f) DMTCl, pyridine
(g) (iPr$_2$N)$_2$POCH$_2$CH$_2$CN, tetrazole, NMI, DMF The azides, compounds 70 and 71 are prepared from the mesylates, compounds 20 and 44 by heating with sodium azide in a polar solvent such as DMF. The amines, compounds 80 and 81 are prepared by reducing compounds 70 and 71 using a trialkylphosphine reagent in a solvent such as methanol. The amines, compounds 80 and 81 are converted to the DMT phosphoramidites, compounds 84 and 85 using the same general procedure illustrated for the preparation of the DMT phosphoramidites, compounds 76 and 77 in Example 20.

Example 23

Preparation of Compound 91

Scheme 9

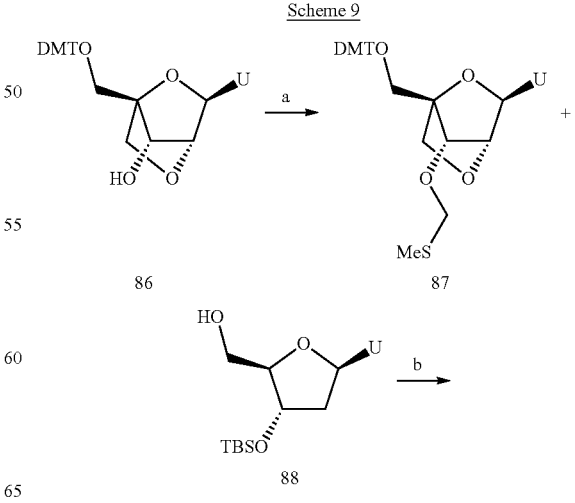

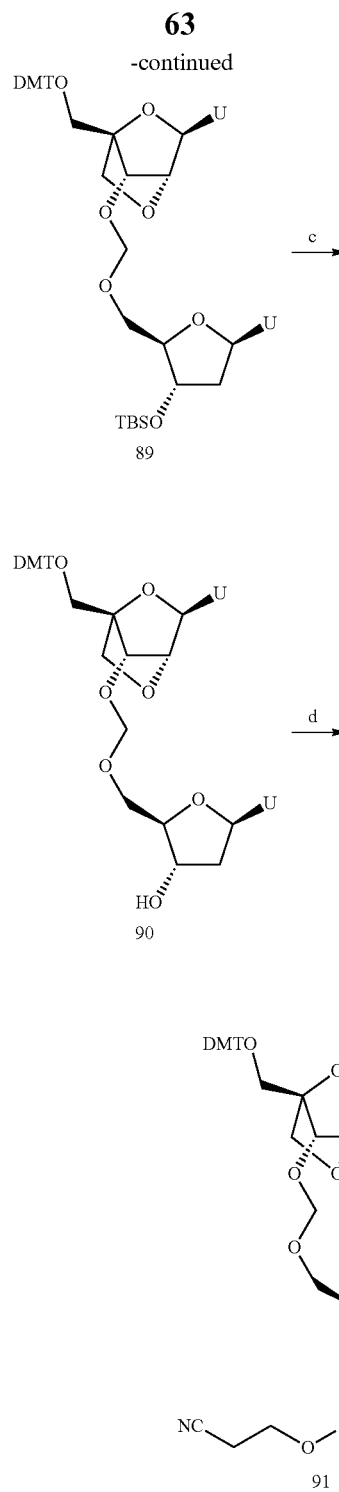

(a) Bz₂O₂, Me₂S
(b) Bromine, benzene
(c) TBAF, THF
(d) (iPr₂N)₂POCH₂CH₂CN, tetrazole, NMI, DMF Compound 87, is prepared from known nucleoside, Compound 86 (Koshkin et al, *J. Org. Chem.* 2001, 66, 8504) and coupled to Compound 88 using the procedures described by Matteucci et al (*J. Org. Chem.* 1993, 58, 2983 and references cited therein) to provide the dimer, Compound 89. The DMT phosphoramidite, Compound 91, is prepared from Compound 89 by means of deblocking the 3'-hydroxyl and phosphitylating the free 3'-hydroxyl using procedures illustrated herein for example in Example 21.

Example 24

Preparation of Compound 95

Scheme 10

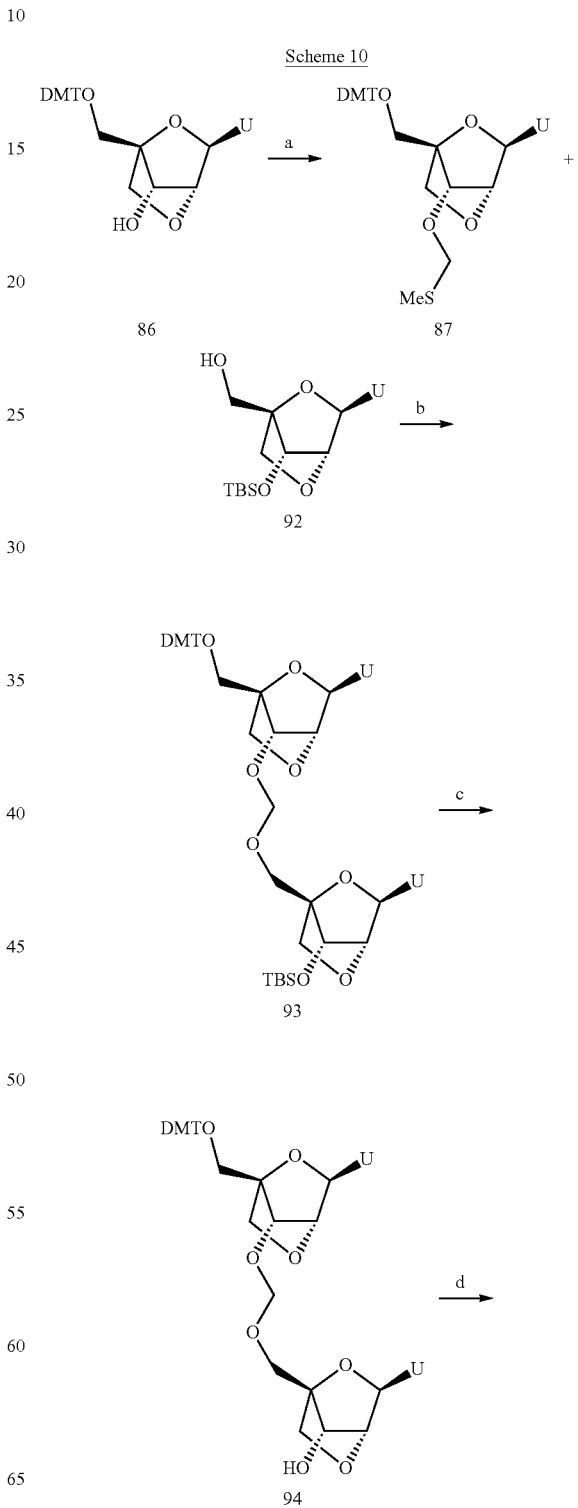

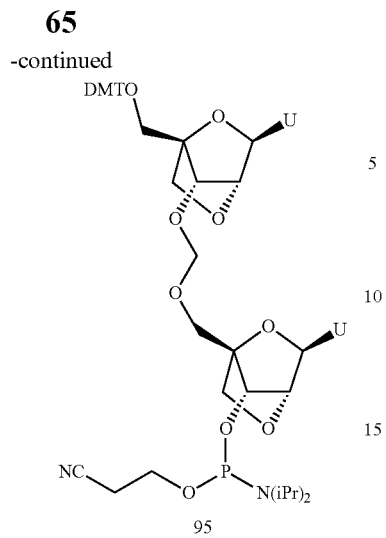

(a) Bz2O2, Me2S
(b) Bromine, benzene
(c) TBAF, THF
(d) (iPr2N)2POCH2CH2CN, tetrazole, NMI, DMF Compound 92 is prepared from known nucleoside, Compound 86 by silylation of the 3'-hydroxyl group with TBSCl in the presence of imidazole using DMF as the solvent. The 5'-O-DMT group is then removed using hexafluoroisopropanol or acetic acid to provide 92. Dimer, Compound 93 is prepared by coupling compounds 87 and 92 using the procedures described by Matteucci et al (*J. Org. Chem.* 1993, 58, 2983 and references cited therein). The DMT phosphoramidite, Compound 95 is prepared from Compound 93 by means of deblocking the 3'-hydroxyl and phosphitylating the free 3'-hydroxyl using procedures illustrated herein for example in Example 21.

Example 25

Preparation of Compound 101

Scheme 11

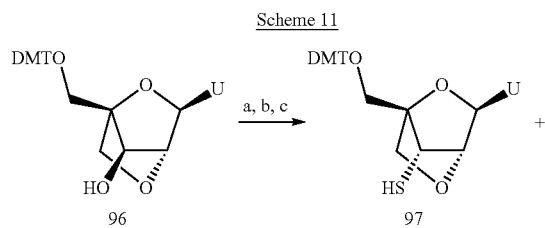

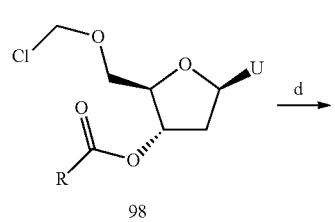

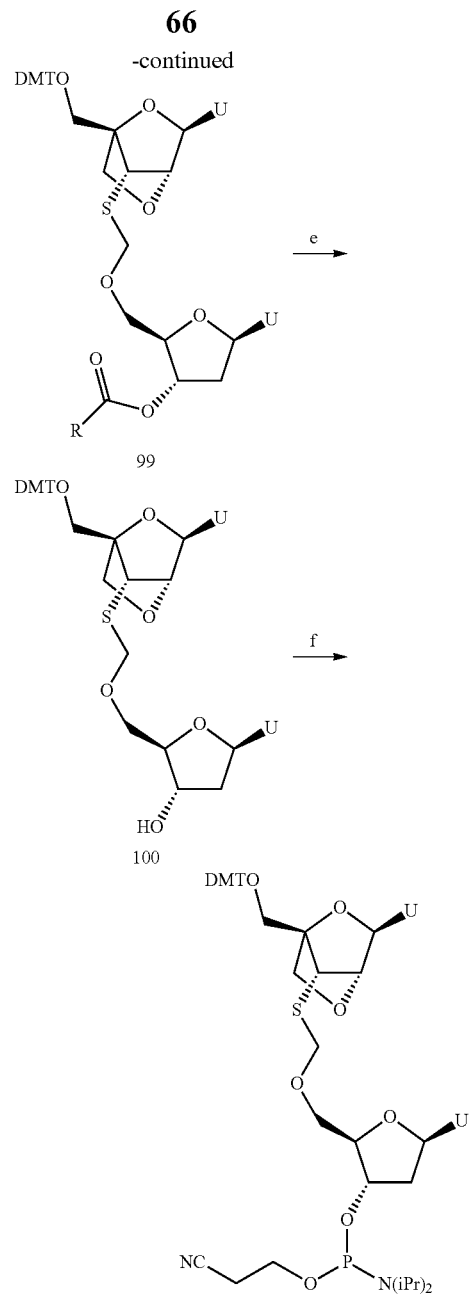

(a) MsCl, DMAP, Et3N, CH2Cl2
(b) KSAc, 18-crown-6, dioxane
(c) Aqueous NH3
(d) DIPEA
(e) NaOMe, MeOH
(f) (iPr2N)2POCH2CH2CN, tetrazole, NMI, DMF Compound 97 is prepared from known nucleoside, Compound 96 (Hakansson et al, *J. Org. Chem.* 2000, 5161) by converting the 3'-hydroxyl group to a leaving group (mesylate, triflate etc), followed by displacement with KSAc and 18-crown-6 in refluxing dioxane or any other suitable solvent. Deprotection of the 3'-thioacetyl group with aqueous ammonia or potassium carbonate in methanol provides Compound 97. The dimer, Compound 100, is prepared from compound 97 and known Compound 98 using the procedures described by Matteucci et al in *J. Org. Chem.* 1993, 58, 2983 and references cited therein. The DMT phosphoramidite, Compound 101, is prepared from nucleoside dimer 100 by means of deblocking the 3'-hydroxyl and phosphitylating the free 3'-hydroxyl using procedures illustrated herein for example in Example 21.

Example 26

Preparation of Compound 105

Scheme 12

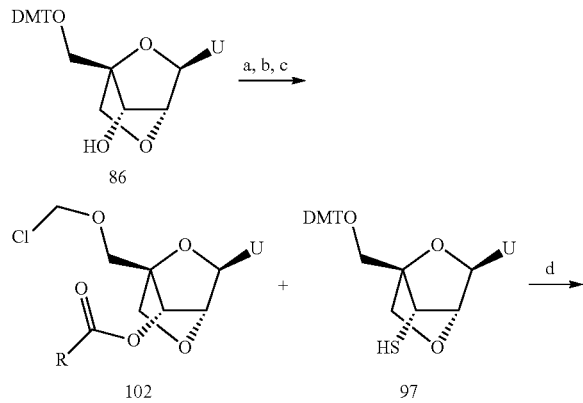

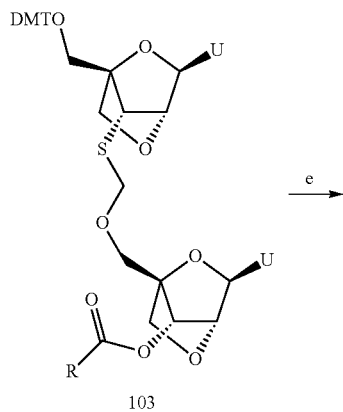

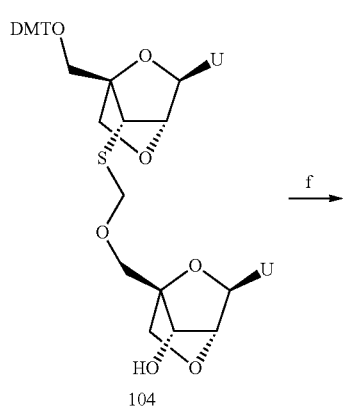

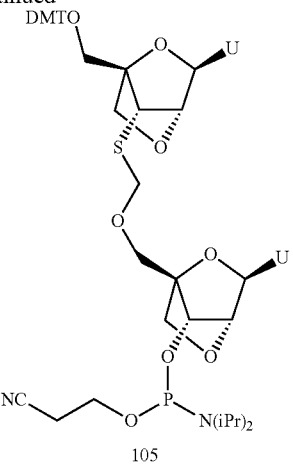

(a) Lauroyl chloride, ET₃N, CH₂Cl₂
(b) Hexafluoroisopropanol
(c) HCHO, HCl
(d) DIPEA
(e) NaOMe, MeOH
(f) (iPr₂N)₂POCH₂CH₂CN, tetrazole, NMI, DMF Compound 102 is prepared form known nucleoside, Compound 86, by acylating the 3'-hydroxyl group followed by removal of the 5' O-DMT group with hexafluoroisopropanol or aqueous acid. Further reaction with HCl and formaldehyde (Matteucci et al in *J. Org. Chem.* 1993, 58, 2983) provides Compound 102. Nucleoside dimer, Compound 104, is prepared by coupling compounds 102 and 97 using the procedures described by Matteucci et al in *J. Org. Chem.* 1993, 58, 2983 and references cited there in. The DMT phosphoramidite, Compound 105, is prepared from nucleoside dimer, Compound 104, by means of phosphitylating the free 3'-hydroxyl using procedures illustrated herein for example in Example 21.

Example 27

1-9-2 gapped oligomers targeted to PTEN: in vivo study

In accordance with the present disclosure, oligomeric compounds were synthesized and tested for their ability to reduce PTEN expression in vivo. Six week old male Balb/c mice (Jackson Laboratory, Bar Harbor, Me.) were administered a single intraperitoneal (i.p) injection of gapped oligomer at 10, 3.2, 1 or 0.32 µmol/kg. Each dose group consisted of four animals. The mice were sacrificed 72 hours following administration. The PTEN mRNA levels in liver were determined using real-time PCR and RIBOGREEN® RNA quantification reagent (Molecular Probes, Inc. Eugene, Oreg.) according to standard protocols. Liver tissues were homogenized and mRNA levels were quantitated using real-time PCR as described herein for comparison to untreated control levels (% UTC). Estimated $ED_{50}$ concentrations for each oligonucleotide were calculated using Graphpad Prism. $ED_{50}$ is the dose at which 50% mRNA reduction is observed.

| SEQ ID NO /ISIS NO | Composition (5'-3') | % UTC @ dose (μmol/kg) | | | | $ED_{50}$ (μmol/kg) | $ED_{50}$ (mg/kg) |
|---|---|---|---|---|---|---|---|
| | | 0.32 | 0.1 | 3.2 | 10 | | |
| 05/402,543 | $U_{l,MMI}GGTCCAGAG^mC_l^mC_l$ | 84 | 52 | 14 | 5.2 | 1.00 | 3.9 |
| 06/396,153 | $T_lGGTCCAGAG^mC_l^mC_l$ | 69 | 21 | 7.0 | 9.2 | 0.50 | 1.9 |

All nucleosides are β-D-2'-deoxyribonucleosides except those followed by a subscript 1 which are bicyclic nucleosides that each have a 4'-$CH_2$—O-2' bridge and $^mC$ indicates a 5-methyl cytosine base. All internucleoside linkages are phosphorothioate except the neutral MMI linkage between the 1 and 2 positions of oligomer 396153, annotated with a subscript MMI.

Liver transaminase levels, alanine aminotranferease (ALT) and aspartate aminotransferase (AST), in serum were also measured relative to saline injected mice. The approximate liver transaminase levels are listed below.

| SEQ ID NO/ ISIS NO | ALT @ 0.32 μmol/kg | ALT @ 1 μmol/kg | ALT @ 3.2 μmol/kg | ALT @ 10 μmol/kg |
|---|---|---|---|---|
| 05/402543 | 55 | 35 | 90 | 2607 |
| 06/396153 | 56 | 60 | 324 | 4031 |

| SEQ ID NO/ ISIS NO | AST @ 0.32 μmol/kg | AST @ 1 μmol/kg | AST @ 3.2 μmol/kg | AST @ 10 μmol/kg |
|---|---|---|---|---|
| 05/402543 | 120 | 71 | 82 | 1239 |
| 06/396153 | 107 | 120 | 234 | 1805 |

Oligonucleotide 402543 containing a MMI linkage has comparable efficacy as compared to oligonucleotide 396153. However, the transaminase levels for 402543 as compared to 396153 indicate that the MMI linkage results in an improved therapeutic index.

The effects on liver, spleen and kidney weights were also determined. Approximate average tissue weights for each treatment group are presented in the table below.

| SEQ ID NO/ ISIS NO | Liver wt. @ 0.32 μmol/kg | Liver wt. @ 1 μmol/kg | Liver wt. @ 3.2 μmol/kg | Liver wt. @ 10 μmol/kg |
|---|---|---|---|---|
| 05/402543 | 1.04 | 1.13 | 1.39 | 1.24 |
| 06/396153 | 1.07 | 1.16 | 1.17 | 1.15 |

| SEQ ID NO/ ISIS NO | Kidney wt. @ 0.32 μmol/kg | Kidney wt. @ 1 μmol/kg | Kidney wt. @ 3.2 μmol/kg | Kidney wt. @ 10 μmol/kg |
|---|---|---|---|---|
| 05/402543 | 1.04 | 1.05 | 1.05 | 1.00 |
| 06/396153 | 1.04 | 1.04 | 1.04 | 1.05 |

| SEQ ID NO/ ISIS NO | Spleen wt. @ 0.32 μmol/kg | Spleen wt. @ 1 μmol/kg | Spleen wt. @ 3.2 μmol/kg | Spleen wt. @ 10 μmol/kg |
|---|---|---|---|---|
| 05/402543 | 1.07 | 0.98 | 0.83 | 0.84 |
| 06/396153 | 1.08 | 0.82 | 0.88 | 1.04 |

| SEQ ID NO/ ISIS NO | Body wt. @ 0.32 μmol/kg | Body wt. @ 1 μmol/kg | Body wt. @ 3.2 μmol/kg | Body wt. @ 10 μmol/kg |
|---|---|---|---|---|
| 05/402543 | 0.98 | 1.10 | 0.93 | 0.94 |
| 06/396153 | 1.00 | 1.03 | 1.09 | 0.95. |

All publications, patents, and patent applications referenced herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A gapped oligomeric compound comprising a contiguous sequence of linked monomeric subunits having two external regions and an internal region including one neutral internucleoside linkage covalently attaching a 3' or 5'-terminal bicyclic nucleoside to the gapped oligomeric compound wherein the gapped oligomeric compound comprises from 12 to 16 linked monomeric subunits and is complementary to at least a portion of a target RNA wherein said neutral internucleoside linkage is a phosphotriester, methylphosphonate, MMI (3'-$CH_2$—N($CH_3$)—O-5'), amide-3 (3'-$CH_2$—C(=O)—N(H)-5'), formacetal (3'-O—$CH_2$—O-5') or a thioformacetal (3'-S—$CH_2$—O-5').

2. The gapped oligomeric compound of claim 1 wherein said neutral internucleoside linkage covalently attaches the bicyclic nucleoside to the 3'-terminus.

3. The gapped oligomeric compound of claim 2 wherein the penultimate nucleoside on the 3'-end of the oligomeric compound is also a bicyclic nucleoside.

4. The gapped oligomeric compound of claim 1 wherein said neutral internucleoside linkage covalently attaches the bicyclic nucleoside to the 5'-terminus.

5. The gapped oligomeric compound of claim 4 wherein the penultimate nucleoside on the 5'-end of the oligomeric compound is also a bicyclic nucleoside.

6. The gapped oligomeric compound of claim 1 wherein said neutral internucleoside linkage is MMI (3'-$CH_2$—N($CH_3$)—O-5'), amide-3 (3'-$CH_2$—C(=O)—N(H)-5'), formacetal (3'-O—$CH_2$—O-5') or thioformacetal (3'-S—$CH_2$—O-5').

7. The gapped oligomeric compound of claim 1 wherein each of said bicyclic nucleoside has formula Ia:

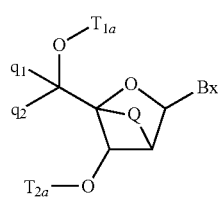

wherein:
Bx is a heterocyclic base moiety;
$T_{1a}$ and $T_{2a}$ are each independently, hydroxyl, a protected hydroxyl, a linked conjugate group, a terminal group, an internucleoside linking group or a neutral internucleoside linking group;
$q_1$ and $q_2$ are each independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

Q is a bivalent bridging group comprising from 1 to 8 linked biradical groups independently selected from —O—, —S—, —N($R_1$)—, —C($R_1$)($R_2$)—, —C($R_1$)=C($R_1$)—, —C($R_1$)=N—, —C(=$NR_1$)—, —Si($R_1$)$_2$—, —$SO_2$—, —SO—, —C(=O)— and —C(=S)—;

each $R_1$ and $R_2$ is, independently, H, hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $NJ_1J_2$, $SJ_1$, $N_3$, $COOJ_1$, acyl (C(=O)—H), substituted acyl, CN, sulfonyl (S(=O)$_2$-$J_1$) or sulfoxyl (S(=O)-$J_1$); and wherein each substituted group comprises one or more optionally protected substituent groups independently selected from halogen, $OJ_1$, $NJ_1J_2$, =$NJ_1$, $SJ_1$, $N_3$, CN, OC(=L)$J_1$, OC(=L)$NJ_1J_2$ and $NJ_3$C(=L)$NJ_1J_2$, wherein each $J_1$, $J_2$ and $J_3$ is, independently, H or $C_1$-$C_6$ alkyl and L is O, S or $NJ_1$.

8. The gapped oligomeric compound of claim 7 wherein Q is 4'-[CH($R_j$)]$_n$—O-2' wherein $R_j$ is H, alkyl or substituted alkyl and n is from 1 to 3.

9. The gapped oligomeric compound of claim 8 wherein $R_1$ is H or methyl.

10. The gapped oligomeric compound of claim 9 wherein n is 1.

11. The gapped oligomeric compound of claim 7 wherein said oligomeric compound further comprises at least one 3' or 5'-linked terminal group.

12. The gapped oligomeric compound of claim 1 wherein each internucleoside linking group that is not a neutral internucleoside linking group is, independently, a phosphodiester or a phosphorothioate.

13. The gapped oligomeric compound of claim 1 wherein each Bx is, independently, uracil, thymine, cytosine, 5-methylcytosine, adenine or guanine.

14. The gapped oligomeric compound of claim 7 comprising at least one region of from 1 to about 5 contiguous bicyclic nucleosides of formula Ia.

15. The gapped oligomeric compound of claim 7 wherein each linked monomeric subunit that is not a bicyclic nucleoside having formula Ia is, independently, a β-D-2'-deoxyribonucleoside or a modified nucleoside.

16. The gapped oligomeric compound of claim 15 wherein each of the modified nucleosides is, independently, a 2'-modified nucleoside, a 4'-thio modified nucleoside or a 4'-thio-2'-modified nucleoside.

17. The gapped oligomeric compound of claim 14 wherein each linked monomeric subunit that is not a bicyclic nucleoside of formula Ia is a β-D-2'-deoxyribonucleoside.

18. The gapped oligomeric compound of claim 7 wherein each external region independently comprises from 1 to 5 contiguous bicyclic nucleosides of formula Ia.

19. The gapped oligomeric compound of claim 18 wherein each monomeric subunit in the internal region is, independently, a β-D-2'-deoxyribonucleoside or a modified nucleoside.

20. The gapped oligomeric compound of claim 19 wherein essentially each monomeric subunit in the internal region is a β-D-2'-deoxyribonucleoside.

21. The gapped oligomeric compound of claim 18 wherein each external region independently comprises from 1 to 3 bicyclic nucleosides of formula Ia.

22. The gapped oligomeric compound of claim 18 wherein each internucleoside linking group that is not a neutral internucleoside linkage is, independently, a phosphodiester or a phosphorothioate.

23. A method comprising contacting a cell with an oligomeric compound of claim 1 wherein said oligomeric compound is complementary to a target RNA.

24. The method of claim 23 wherein said cell is in a human.

25. The method of claim 23 wherein said target RNA is selected from mRNA, pre-mRNA and micro RNA.

26. The method of claim 23 further comprising evaluating the antisense activity of said oligomeric compound on said cell wherein said evaluating comprises detecting the levels of target RNA and or a protein.

* * * * *